United States Patent
Beck

(10) Patent No.: US 10,010,372 B1
(45) Date of Patent: Jul. 3, 2018

(54) MARKER POSITIONING APPARATUS

(71) Applicant: Paul Beck, Atlanta, GA (US)

(72) Inventor: Paul Beck, Atlanta, GA (US)

( * ) Notice: Subject to any disclaimer, the term of this patent is extended or adjusted under 35 U.S.C. 154(b) by 257 days.

(21) Appl. No.: 15/205,880

(22) Filed: Jul. 8, 2016

Related U.S. Application Data

(63) Continuation-in-part of application No. 14/989,437, filed on Jan. 6, 2016.

(51) Int. Cl.
| | |
|---|---|
| *A61B 6/00* | (2006.01) |
| *A61B 34/10* | (2016.01) |
| *A61B 6/03* | (2006.01) |
| *A61B 90/00* | (2016.01) |

(52) U.S. Cl.
CPC .............. *A61B 34/10* (2016.02); *A61B 6/032* (2013.01); *A61B 6/4452* (2013.01); *A61B 6/487* (2013.01); *A61B 6/505* (2013.01); *A61B 6/547* (2013.01); *A61B 6/585* (2013.01); *A61B 90/39* (2016.02); *A61B 2034/107* (2016.02); *A61B 2034/108* (2016.02); *A61B 2090/3966* (2016.02)

(58) Field of Classification Search
CPC ..................................................... A61B 90/39
See application file for complete search history.

(56) References Cited

U.S. PATENT DOCUMENTS

| | | | |
|---|---|---|---|
| 5,360,446 A | 11/1994 | Kennedy | |
| 5,400,513 A | 3/1995 | Duffield | |
| 5,682,886 A | 11/1997 | Delp et al. | |
| 5,769,092 A | 6/1998 | Williamson, Jr. | |
| 5,799,055 A | 8/1998 | Peshkin et al. | |
| 5,832,422 A | 11/1998 | Wiedenhoefer | |
| 6,205,411 B1 | 3/2001 | Digioia et al. | |
| 6,229,869 B1 | 5/2001 | Hu | |
| 6,272,247 B1 | 8/2001 | Manickam et al. | |

(Continued)

FOREIGN PATENT DOCUMENTS

EP 2405336 11/2012

OTHER PUBLICATIONS

International Searching Authority, International Search Report and Written Opinion dated Mar. 31, 2017, issued in connection with International Application No. PCT/US2017/012012, filed Jan. 3, 2017, 12 pages.

(Continued)

*Primary Examiner* — Dani Fox
(74) *Attorney, Agent, or Firm* — McDonnell Boehnen Hulbert & Berghoff LLP

(57) ABSTRACT

An apparatus for positioning calibration markers may include an extension arm connected to one or more radio-dense calibration markers. The apparatus may also include a mounting device removably attachable to a radiographic imaging device and coupled to the extension arm. The mounting device may provide for translation of the extension arm with respect to the radiographic imaging device in at least a first dimension. The apparatus may additionally include one or more visual alignment features on the mounting device. The one or more visual alignment features may be configured to align the one or more radio-dense calibration markers relative to the radiographic imaging device. The translation of the extension arm may repositions the one or more radio-dense calibration markers with respect to the radiographic imaging device.

20 Claims, 23 Drawing Sheets

(56) References Cited

U.S. PATENT DOCUMENTS

| | | | |
|---|---|---|---|
| 6,334,157 | B1 | 12/2001 | Oppermann et al. |
| 6,342,905 | B1 | 1/2002 | Diedrich et al. |
| 6,424,332 | B1 | 7/2002 | Powell |
| 6,459,948 | B1 | 10/2002 | Ateshian et al. |
| 6,573,915 | B1 | 6/2003 | Sivan et al. |
| 6,585,412 | B2 | 7/2003 | Mitschke |
| 6,701,174 | B1 | 3/2004 | Krause et al. |
| 6,772,026 | B2 | 8/2004 | Bradbury et al. |
| 6,932,842 | B1 | 8/2005 | Litschko et al. |
| 7,158,692 | B2 | 1/2007 | Chalana et al. |
| 7,383,073 | B1 | 6/2008 | Abovitz et al. |
| 7,388,972 | B2 | 6/2008 | Kitson |
| 7,468,075 | B2 | 12/2008 | Lang et al. |
| 7,534,263 | B2 | 5/2009 | Burdulis, Jr. et al. |
| 7,981,158 | B2 | 7/2011 | Fitz et al. |
| 7,983,777 | B2 | 7/2011 | Melton et al. |
| 8,066,708 | B2 | 11/2011 | Lang et al. |
| 8,077,950 | B2 | 12/2011 | Tsougarakis et al. |
| 8,712,715 | B2 * | 4/2014 | Tonami et al. ............... 702/104 |
| 8,908,937 | B2 | 12/2014 | Beck |
| 8,917,290 | B2 | 12/2014 | Beck |
| 9,433,390 | B2 * | 9/2016 | Nathaniel et al. ............ 382/131 |
| 2002/0080913 | A1 | 6/2002 | Roder |
| 2004/0151399 | A1 | 8/2004 | Skurdal et al. |
| 2005/0038338 | A1 | 2/2005 | Bono et al. |
| 2005/0059873 | A1 | 3/2005 | Glozman et al. |
| 2005/0162419 | A1 | 7/2005 | Kim et al. |
| 2006/0242159 | A1 | 10/2006 | Bishop et al. |
| 2006/0287733 | A1 | 12/2006 | Bonutti |
| 2007/0118055 | A1 | 5/2007 | McCombs |
| 2007/0118243 | A1 | 5/2007 | Schroeder et al. |
| 2007/0198022 | A1 | 8/2007 | Lang et al. |
| 2007/0226986 | A1 | 10/2007 | Park et al. |
| 2007/0272747 | A1 | 11/2007 | Woods et al. |
| 2008/0063302 | A1 | 3/2008 | Russak et al. |
| 2008/0063304 | A1 | 3/2008 | Russak et al. |
| 2008/0148167 | A1 | 6/2008 | Russak et al. |
| 2008/0180406 | A1 | 7/2008 | Han et al. |
| 2008/0189358 | A1 | 8/2008 | Charles |
| 2008/0319448 | A1 | 12/2008 | Lavallee et al. |
| 2009/0043556 | A1 | 2/2009 | Axelson et al. |
| 2009/0089081 | A1 | 4/2009 | Haddad |
| 2009/0222014 | A1 | 9/2009 | Bojarski et al. |
| 2009/0259967 | A1 | 10/2009 | Davidson et al. |
| 2009/0306676 | A1 | 12/2009 | Lang et al. |
| 2009/0312805 | A1 | 12/2009 | Lang et al. |
| 2010/0030231 | A1 | 2/2010 | Revie et al. |
| 2010/0080491 | A1 | 4/2010 | Ohnishi |
| 2010/0134425 | A1 | 6/2010 | Storrusten |
| 2010/0135467 | A1 * | 6/2010 | King et al. .................... 378/163 |
| 2010/0217270 | A1 | 8/2010 | Polinski et al. |
| 2010/0274534 | A1 | 10/2010 | Steines et al. |
| 2010/0281678 | A1 | 11/2010 | Burdulis, Jr. et al. |
| 2010/0295803 | A1 | 11/2010 | Kim et al. |
| 2010/0303313 | A1 | 12/2010 | Lang et al. |
| 2010/0303317 | A1 | 12/2010 | Tsougarakis et al. |
| 2010/0303324 | A1 | 12/2010 | Lang et al. |
| 2010/0305907 | A1 | 12/2010 | Fitz et al. |
| 2010/0329530 | A1 | 12/2010 | Lang et al. |
| 2011/0029091 | A1 | 2/2011 | Bojarski et al. |
| 2012/0008848 | A1 | 1/2012 | Beck |
| 2012/0194505 | A1 | 8/2012 | Beck |
| 2015/0216498 | A1 | 6/2015 | Schulze et al. |

OTHER PUBLICATIONS

Anonymous, "Iconico Screen Calipers," Jan. 2, 2010, 16 pages, retrieved from the internet: URL: http://web.archiv.org/web/20100102043404/http://iconico.com/caliper/index.aspx [retrieved on Oct. 20, 2011].

Brannigan et al., "A Framework for "Need to Know" Authorizations in Medical Computer Systems: Responding to the Constitutional Requirements," JAMIA, Proceedings of the 18th Annual Symposium on Computer Applications in Medical Care, 1994, pp. 396-396.

King, Richard et al., "A novel method of accurately calculating the radiographic magnification of the hip," Warwick Orthopaedics, 2009.

Kosashvili et al., "Digital versus conventional templating techniques in preoperative planning for total hip arthoplasty," Can J Surgery, 2009, pp. 6-11, vol. 52, No. 1.

Michalikova et al., "The Digital Pre-Operative Planning of Total Hip Arthroplasty," Acta Polytechnica Hungarica, 2010, vol. 7, No. 3.

Moscovich et al., "Multi-finger cursor techniques," Proc. GI'06, Toronto: CIPS, 2006, pp. 1-7.

Murzic et al., "Digital Templating in Total Hip Replacement," US Musculoskeletal Review, 2006.

OrthoView, "Joint Arthroplasty Digital Orthopaedic Templating & Planning," 7 pages accessed Jan. 7, 2016, http://www.orthoview.com/product/joint-replacement.

OrthoView, "OrthoView Digital Pre-operative Planning Tools & Wizards," 5 pages accessed Jan. 7, 2016, http://www.orthoview.com/about/planning-software/scaling.

OrthoView, "Scaling Orthopaedic Digital X-rays in OrthoView Templating Software," 7 pages, accessed Jan. 7, 2016, http://www.orthoview.com/about/planning-software/scaling.

OrthoView, Orthopaedic Digital Templates for Pre-operative Planning, http://www.orthoview.com/about/planning-software/orthopaedic-templates, 2016.

Project SIKULI, http://www.sikuli.org/, accessed on Jan. 7, 2016, 2 pages.

Screen Capture Software for Windows, Mac and Chrome—Snagit, 7 pages, accessed Jan. 7, 2016, https://www.techsmith.com/snagit.html.

Steinberg et al., "Preoperative planning of total hip replacement using the TraumaCad system," Archives of Orthopaedic and Trauma Surgery: Including Arthroscorpy and Sports Medicine, Jan. 13, 2010, pp. 1429-1432, vol. 130, No. 12.

"TraumaCad User's Guide Version 2.2," Voyant Health, A Voyant Helath Ltd. Documents, 2010, 206 pages.

TraumaCad Touch New! and Trauma Cad OrthoWeb, Voyant Health, Dec. 2009, 2 pages, MK200197_B.

TraumaCad Touch Guide, BrainLAB's Digital Lightbox, Orthocrat, www.orthocrat.com, 12 pages.

Wikipedia, "Screenshot," May 22, 2009.

Wikipedia, "Distributed Computing," Jan. 5, 2009.

Wikipedia, "Metadata," May 29, 2009.

Wikipedia, "HUD (video gaming)," Dec. 6, 2009.

Wikipedia, "Photogrammerty," Jul. 7, 2010.

Yusof et al., "Devolpement of Total Knee Replacement Digital Tempmlating Software," Visual Infomatics: Bridging Research and Practice, Springer Berlin Heidelberg, Berlin, Heidelberg, Nov. 11, 2009, pp. 180-190.

European Patent Office, European Search Report dated Nov. 10, 2011, issued in connection with EP Application No. 11172626.

Steven Delalio, "Xemarc Offers Adhesive Pads Used for Measurement Calibration Marker (MCM) Ball Attachment," 2 pages accessed Jul. 8, 2016, http://www.prweb.com/releases/2006/06/prweb396859.htm.

CE4RT, "Radiography for Joint Replacement Using Calibration Markers," 6 pages accessed Jul. 8, 2016, https://ce4rt.com/positioning/117-radiography-for-joint-replacement-using-markers.

* cited by examiner

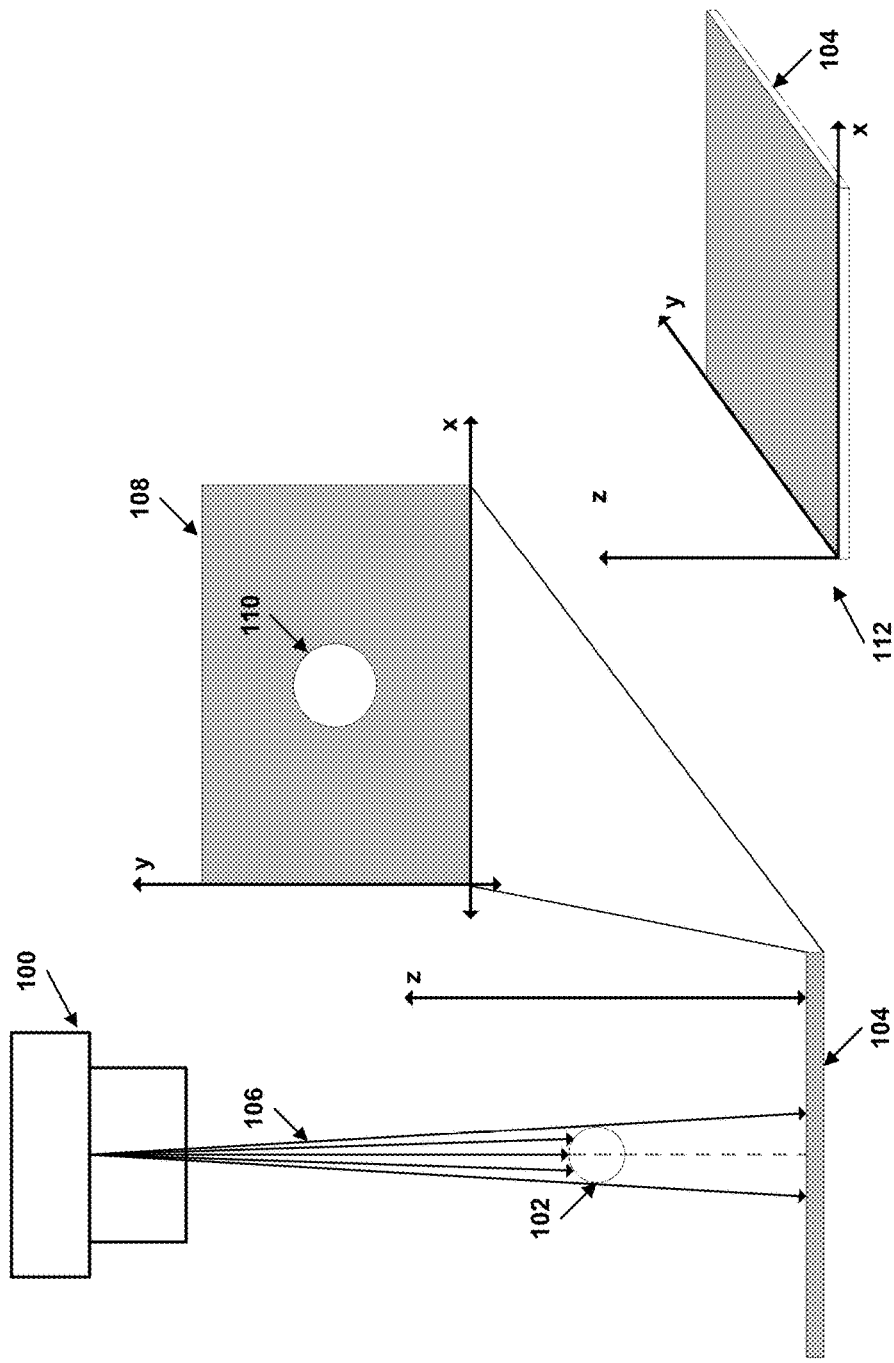

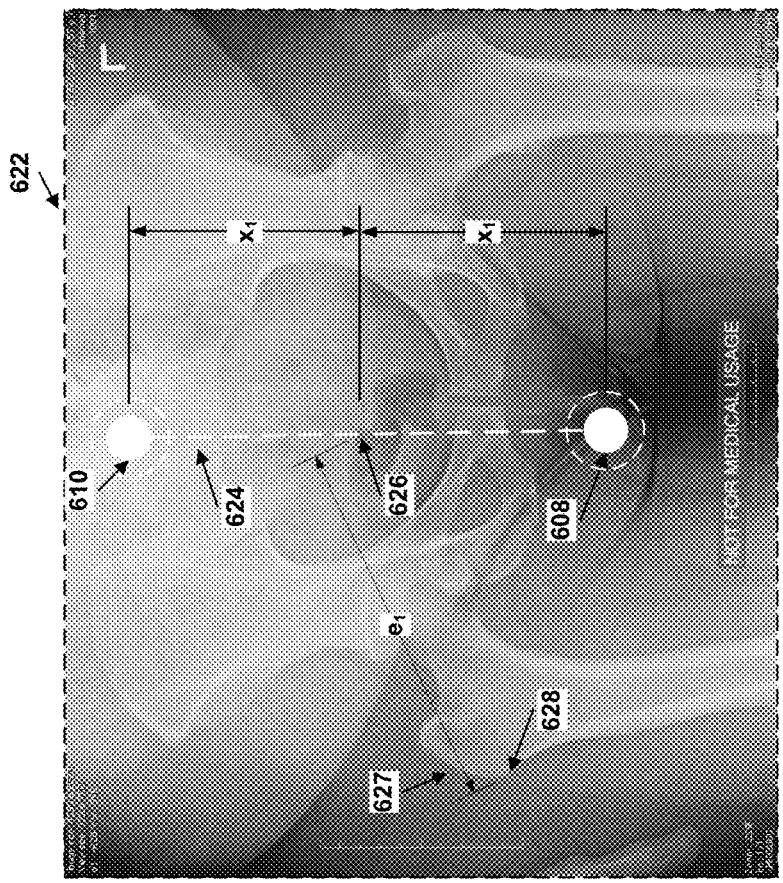
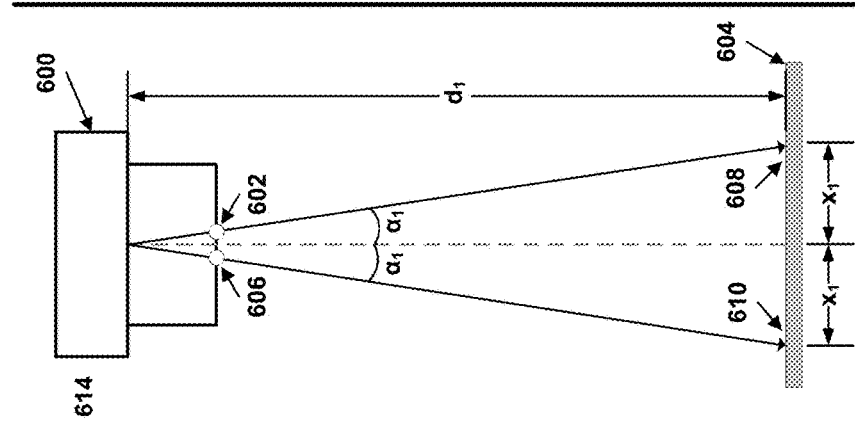
Fig. 6D
Fig. 6C

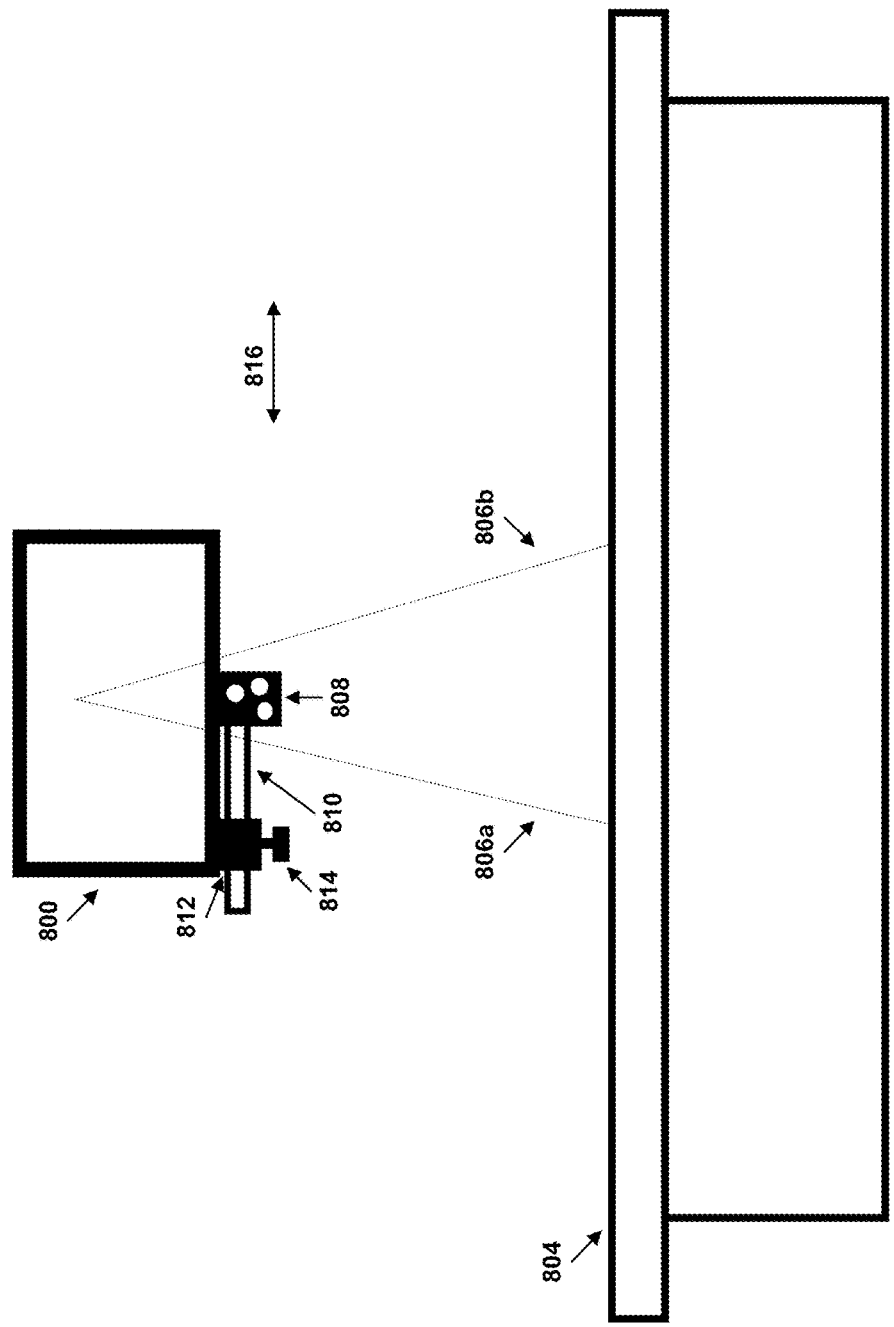

MARKER POSITIONING APPARATUS

CROSS REFERENCE TO RELATED APPLICATIONS

The present application is a continuation-in-part of and claims priority to U.S. patent application Ser. No. 14/989,437 filed on Jan. 6, 2016 and entitled "Accurate Radiographic Calibration Using Multiple Images" which is herein incorporated by reference as if fully set forth in this description.

BACKGROUND

Orthopedic joint replacement surgeries such as hip replacement and knee replacement typically involve replacing a damaged bone or joint with a prosthetic implant. Similarly, orthopedic stabilization surgeries involve bracing or fixating an injured bone so that it heals properly. The prosthetic implant or brace is shaped in a way that allows movement similar to that of a healthy joint.

In order for an orthopedic replacement procedure to be successful, a physician anticipates both the size and shape of the prosthetic implant that will most closely match the anatomy of the patient. This is often done based on radiographic (i.e., X-ray) images of the patient's joint and the associated bone structure. If the size and shape are estimated incorrectly, the necessary prosthetic implant might be unavailable during surgery. A prosthesis of incorrect size might be implanted, leading to complications.

SUMMARY

Described herein are devices for positioning one or more radio-dense markers with respect to a radiographic imaging device. The radiographic imaging device may be an X-Ray device that includes a radiation source and a radiation receiver. Alternatively, the radiographic imaging device may be a computer tomography (CT) device and/or a fluoroscopy device. Other radiographic imaging devices are possible. The device for positioning the radio-dense markers includes an extension arm connected to the radio-dense markers. The extension arm is connected to a mounting device that is removably attachable to the radiographic imaging device. For example, the mounting device may attach to the radiation source or the radiation receiver.

The positioning device may further include a post connecting the extension arm to the mounting device. The extension arm may be configured to move in a first dimension relative to the radiation receiver and the mounting device. The position of the mounting device may be adjustable in a second dimension with respect to the radiographic imaging device. A length of the post may be adjustable to control a distance between the mounting device and the extension arm. The length of the post may be adjustable in a third dimension. The first, second, and third dimension may be orthogonal to one another, thus allowing complete control over the position of the calibration markers in three dimensions.

A first fastening mechanism may be included to lock in a particular position of the extension arm with respect to the radiographic imaging device in the first dimension. A second fastening mechanism may be included to lock in a particular position of the mounting device with respect to the radiographic imaging device in the second dimension. A third fastening mechanism may be included to lock in a particular height of the post with respect to the radiographic imaging device in the third dimension.

In one example, an apparatus is provided that includes an extension arm connected to one or more radio-dense calibration markers. The apparatus also includes a mounting device removably attachable to a radiographic imaging device and coupled to the extension arm. The mounting device provides for translation of the extension arm with respect to the radiographic imaging device in at least a first dimension. The apparatus additionally includes one or more visual alignment features on the mounting device. The one or more visual alignment features are configured to align the one or more radio-dense calibration markers relative to the radiographic imaging device. The translation of the extension arm repositions the one or more radio-dense calibration markers with respect to the radiographic imaging device.

In another example, a means for positioning marking means is provided that includes an extension arm connected to one or more radio-dense marking means. The means for positioning marking means also includes a mounting means removably attachable to a radiographic imaging device and coupled to the extension arm. The mounting means provides for translation of the extension arm with respect to the radiographic imaging device in at least a first dimension. The means for positioning marking means additionally includes visual alignment means on the mounting means. The visual alignment means is configured to align the one or more radio-dense marking means relative to the radiographic imaging device. The translation of the extension arm repositions the one or more radio-dense marking means with respect to the radiographic imaging device.

In a further example, an embodiment is provided that includes positioning a radiation source and a radiation receiver in a first orientation with respect to one another. The embodiment also includes positioning an extension arm connected to one or more radio-dense calibration markers to align, in at least a first dimension, one or more alignment features of the extension arm with at least one of the radiation source or the radiation receiver. The example embodiment additionally includes positioning a mounting device to align, in at least a second dimension perpendicular to the first dimension, one or more alignment features of the mounting device with at least one of the radiation source or the radiation receiver. The mounting device removably attaches the extension arm to at least one of the radiation source or the radiation receiver. The embodiment further includes adjusting a length of a post coupling the extension arm to the mounting device to position the one or more calibration markers in a third dimension with respect to at least one of the radiation source or the radiation receiver. The third dimension is perpendicular to the first dimension and the second dimension.

BRIEF DESCRIPTION OF THE DRAWINGS

FIG. 1A illustrates a radiation source positioned above a receiver, according to an example embodiment.

FIG. 1B illustrates a coordinate system attached to a receiver, according to an example embodiment.

FIGS. 6C, 6D, and 6E illustrate an alternative approach of determining a height of an object of interest, according to an example embodiment.

FIG. 8 illustrates an example marker positioning device connected to a radiation source, according to an example embodiment.

DETAILED DESCRIPTION

Figure 2A:
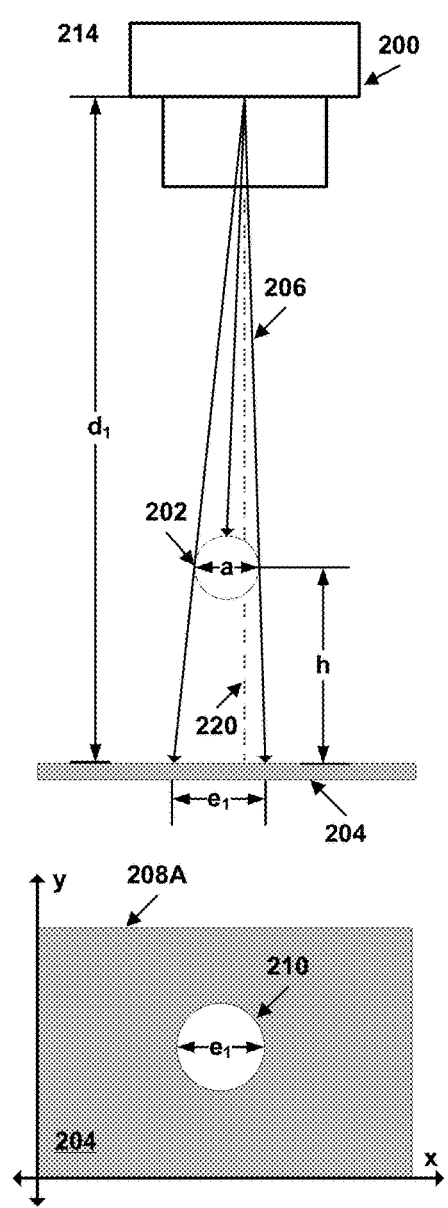
FIGS. 2A and 2B illustrate the acquisition of radiographs from different vertical and horizontal radiation source positions and angular orientations, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. Overview

In the field of medicine, it is often useful to identify the magnification of an object or objects (e.g., blood vessels, tumors, bones, hardware implants) within a radiograph or a representation of a radiograph. Knowing the magnification of different body parts within a radiograph enables medical professionals to determine their actual physical size.

For example, in orthopedic surgery, medical professionals often measure the size of multiple objects including hardware implants, bones, joints and bone lesions. This enables the medical professional to determine: 1) if a bone lesion has changed in size, 2) a fracture has significantly displaced, or 3) what type and size of hardware is required to reconstruct a joint, a bone, or stabilize a fracture.

In order for an orthopedic replacement procedure to be successful, a physician may need to anticipate both the size and shape of the prosthetic implant that will most closely match the anatomy of a patient. Traditionally, the physician may manually size implants based on radiographs of the patient's joint and the associated bone structure. The physician may place a clear sheet, called a template, containing an outline in the size and shape of the prosthetic implant over the radiograph. The template may include anatomical reference markings. Given that radiographs and the images contained therein are typically magnified by approximately 10% to 25%, the template is also typically magnified to account for the anticipated magnification of the patient's bone structure when a radiograph is taken.

Using multiple templates in a trial-and-error fashion, the physician may eventually select a size for the prosthetic implant. However, as different anatomical features of a joint are located at different heights, they are magnified to a different extent. Additionally, radiographic magnification also varies among people with different body habitus (e.g., obese, very muscular). Unfortunately, the traditional templating process only approximates the magnification for the radiograph and assumes that this approximation applies equally to all anatomical features depicted in the radiograph. As a result, the traditional approach may result in the selection of a prosthetic implant of the wrong size.

In order to overcome this problem, some physicians place a sizing marker on the radiograph that enables them to more accurately determine the magnification of the radiograph and the images contained therein. Once the radiograph has been templated, the physician then adjusts the selected prosthesis size by the determined magnification. However, since the template is not resized to the correct magnification prior to being placed over the radiograph, the incorrectly sized template can be placed in the incorrect position. Accordingly, using a sizing marker does not improve the accuracy of the templating process.

With the introduction of digital imaging, traditional templating is being replaced by digital templating. With digital templating, the physician views a representation of the radiograph on a computer and uses a digital representation of the template to select a replacement prosthesis closest in size and shape to the anatomical features of the patient. Digital templating has a significant advantage over traditional methods in that digital templates are not limited to one size magnification. Templating software enables either the templates or the radiograph to be adjusted to the correct magnification prior to placement of the template. However, digital templating still has one major weakness. Namely, it does not have a reliable and reproducible method of determining the magnification of an object image or object images within a radiograph. As a result, despite the advantages of software, it is often just as inaccurate as templating using traditional template overlays.

To determine the magnification of an object image within a radiograph, a calibration process is required that precisely determines the height of that object above a radiographic receiver at the time when the radiograph was obtained. Unfortunately, as described below, existing methods are not reliable as some of them depend on marker placement by a medical professional at an estimated height of an object deep within the human body. Not only is this method fraught with human error, the error is not readily identifiable while a user is templating the object image within the radiograph. Thus, the user might not know if the templating results are accurate.

Additional weaknesses exist with current methods of calibration. Present methods of calibration apply the same scaling factor to all object images within a radiograph as they do not have a way of determining the height of different objects of interest depicted within a radiograph. As a result, multiple objects cannot be templated accurately as they are often at different heights than the calibration marker.

Finally, when only a single magnification factor is applied across the entire radiograph, additional information such as the rotational position of an object depicted within the radiograph cannot be determined. Since joint and bone rotation often determine the shape of template chosen, without knowing the rotation of the joint at the time the radiograph was taken, the selected prosthetic implant often does not accurately reflect the anatomy of the patient's joint.

Health care providers (e.g., hardware manufacturers, hospital systems, and medical professionals) have attempted to leverage the preoperative measurement capabilities of digital templating to reduce the cost of care and improve patient outcomes. In particular, accurately determining the size of a bone or joint prior to surgery may improve patient outcomes and reduce the cost of supplying medical hardware to the operating room by narrowing the range of hardware that needs to be available on-hand during surgery. Manufacturers of the medical hardware may consequently produce, transport, and store less hardware. Likewise, hospital systems may keep fewer products on the shelf and may reduce surgical cost associated with preoperative hardware management and operative time. Additionally, accurate preoperative measurements may reduce surgical time and facilitate a significant reduction in operative complications by providing hardware that most closely matches the size and shape of a patent's anatomical features.

Determining the actual physical size of a patient's anatomical features (e.g., bones and bone features) may be of notable importance in a cost-conscious medical environment for additional reasons. In particular, as hospital systems attempt to reduce costs by decreasing the hardware and accessories available off the shelf in the operating room, the correct hardware may be unavailable intraoperatively if the size and shape of the patient's anatomical features were not accurately determined prior to surgery. Similarly, if a patient has abnormally sized joints or is an unusual variant with respect to body composition, off-the-shelf hardware may not match the patient's anatomy and the patient may require customized replacement hardware. If the size of the patient's anatomical features is not determined accurately, the customized hardware may not be a good fit.

Inaccurate preoperative templating may prolong surgery and may cause a surgeon to place incorrectly sized hardware on the patient, leading to complications. Complications may include, but are not limited to, non-healing, chronic pain, deformity, instability, nonvascular injury, deep venous thrombosis, pulmonary embolus, infection, and/or cardiac/respiratory compromise. Additionally, surgically implanting an oversized prosthesis in a patient may result in an increased incidence of femoral fracture, excess leg length, or nerve palsy. Conversely, hardware loosening, shortened leg length, or hip dislocation may result from implanting undersized hardware.

As described herein, the magnification of an image of an object of interest in a radiograph may be determined by using at least two different radiographs, each radiograph captured from a different orientation. In contrast to existing digital templating solutions, this approach is not limited to applying the same level of magnification to images corresponding to different objects of interest contained within the same radiograph. A plurality of levels of magnification may be determined, each corresponding to a different anatomical feature or object of interest, the images of which may be contained within a radiograph.

Additionally, the position and orientation of multiple objects may be determined based on at least two different radiographs. For example, the degree of femoral anteversion or retroversion may be determined based on at least two different radiographs, each acquired from a different perspective. This approach may enable accurate measurement by placing templates at a rotation that substantially matches the determined rotation of the femur at the time of capturing the radiograph. As a result, no special patient positioning is required. The apparatuses and operations described herein are not limited to the hip and femur but may also be used for any body part of interest.

In general, the devices and operations herein described are not limited to applications in digital templating. The devices and operations herein described may be used with any type of medical procedure or aid any type of medical diagnosis that includes radiographic imaging. For example, the devices and operations may be used in the design and selection of orthopedic cutting guides, drill guides, and other patient-specific three-dimensional printed elements.

II. Example Radiographic Devices

FIG. 1A depicts an example arrangement of a radiation source 100 positioned above a radiation receiver 104. The radiation source 100 and the radiation receiver 104 may be collectively referred to as a radiographic imaging device. Other arrangements of radiographic imaging devices may be possible. An object of interest 102 is shown positioned between the radiation source 100 and receiver 104. A radiograph 110 of the object of interest is shown in the top view 108 of receiver 104. The object 102 may be a part of a human body, such as the head of a femur or the head of a humerus. In general, the object 102 may be any physical structure not limited to bones or parts of the human body. The receiver 104 may be any type of film, material, or device that, when exposed to radiation 106 from source 100, results in the creation of an image 110 of object 102. The receiver 104 may also be referred to as a cassette or detector. In some embodiments, the radiation source 100 and radiation receiver 104 may both be rotated by 90 degrees such that the radiation 106 projected from radiation source 100 travels horizontally with respect to the ground.

The diameter of image 110 is larger than the diameter of object 102. In other words, the image 110 is a magnified (enlarged) representation of the object 102. The embodiments described herein are directed at determining the level of magnification of the image 110 of object 102 so that the image 110 can be used to accurately represent the actual physical size of object 102. Determination of the level of magnification may rely on one or more calibration markers that may be positioned with respect to the radiographic imaging device using one or more of the example calibration marker positioning devices/apparatuses described herein.

FIG. 1B illustrates an example coordinate system 112 attached to receiver 104. The coordinate system 112 is a Cartesian coordinate system comprising an x-axis corresponding to a width of image 110, a y-axis corresponding to a length of image 110, and a z-axis corresponding to a height of objects (e.g., object 102) above the receiver 104. Some embodiments may alternatively utilize a polar coordinate system, a cylindrical coordinate system, a spherical coordinate system, or any combination thereof. Other choices of coordinate systems are possible. Some embodiments may chose a coordinate system that simplifies the computation required to determine the magnification of image 110.

In general, the embodiments described herein involve measuring and/or determining the relative position between the radiation source 100 and the receiver 104, the object 102 and the receiver 104, the radiation source 100 and the object 102, and/or the image 110 and the receiver 104. The relative positions may be used to determine the magnification of images of corresponding objects of interest within radiographs.

Figure 2B:
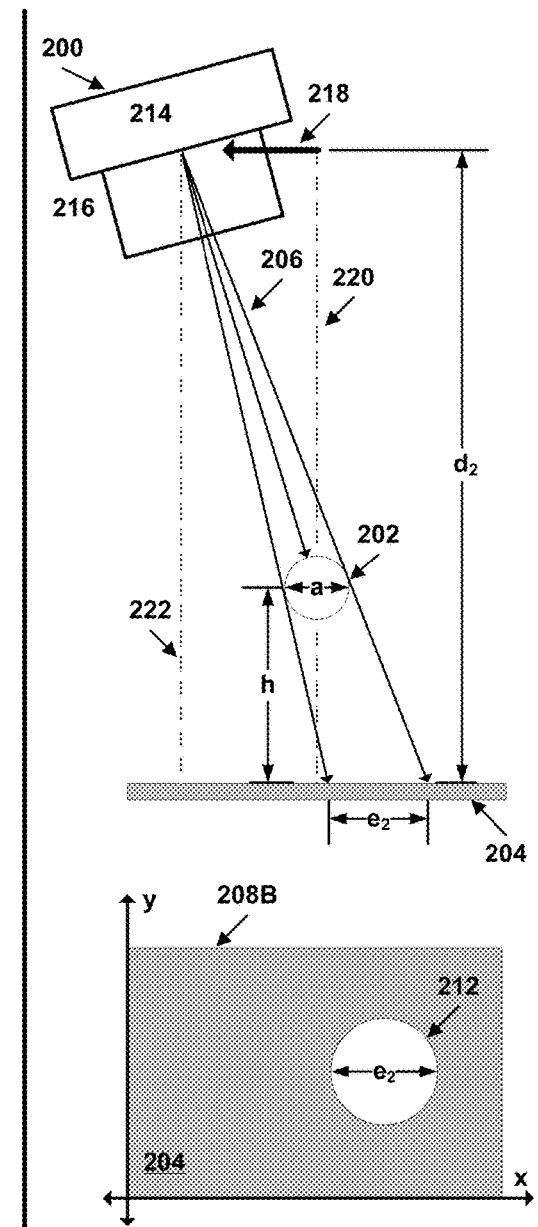

FIGS. 2A and 2B illustrate an example embodiment where a magnification of an object of interest may be determined based on two radiographs. Specifically, the magnification of first image 210 and/or second image 212 of the object of interest 202 may be determined based on a relative position and/or orientation between radiation source 200 and radiation receiver 204. The second image 212 may be captured while the vertical and horizontal positions of the radiation source 200 are different from the vertical and horizontal positions of the radiation source 200 used to capture the first image 210. FIG. 2B additionally shows the radiation source 200 rotated relative to its original orientation in FIG. 2A. The radiation source 200 may be rotated to ensure that the emitted radiation 206, or at least a portion thereof, is aimed at the object of interest 202. However, the radiation source 200 may also be rotated to take a second image 212 from a different perspective than image 210. While FIG. 2B shows the radiation source 200 in a rotated position relative to the position illustrated in FIG. 2A, alternative embodiments may be practiced without rotating the radiation source 200.

In general, although FIG. 2B illustrates the radiation source 200 translated vertically, translated horizontally, and rotated relative to the position 214 in FIG. 2A, alternative embodiments may function by performing only one of the described movements. For example, some embodiments may involve only horizontal translation of the radiation source 200 or both horizontal translation and rotation of the radiation source 200. In alternative embodiments, the radiation receiver 204 may be moved while the radiation source 200 is held in a fixed position. The embodiment illustrated by FIGS. 2A and 2B includes all three movement types (horizontal translation, vertical translation, and rotation) for the purpose of providing a generalized example geometric model.

Furthermore, although the example diagrams are two-dimensional, the embodiments described herein are equally applicable to three dimensions. For example, a different perspective of the object of interest may be achieved via horizontal translation in the x-direction, horizontal translation in the y-direction, vertical translation in the z-direction, rotation along the pitch-axis, rotation along the roll-axis, or any combination thereof, provided that the geometry of the changed perspective is properly accounted for, as demonstrated herein.

III. Example Operations for Determining Object Height and Magnification

FIG. 2A illustrates radiation source 200 located a distance $d_1$ above the receiver 204. The radiation source 200 emits radiation 206, which creates an image 210, as illustrated in the top view 208A of receiver 204. The top view 208A may also represent the radiograph produced when object 202 is exposed to radiation 206 from radiation source 200 when radiation source 200 is at position 214. The image 210 has a diameter $e_1$. Line 220 illustrates the x-position of the radiation source 200 above receiver 204. After acquisition of image 210, the radiation source 200 may be moved from position 214 to position 216 as shown in FIG. 2B. In FIG. 2B, the radiation source 200 is located a distance $d_2$ above the receiver 204 at position 216. Additionally, the radiation source 200 has been translated horizontally to the left as indicated by arrow 218. The difference in x-position of line 220 and line 222 illustrates the extent of horizontal translation.

In FIG. 2B, radiation source 200 emits radiation 206 which creates an image 212, as illustrated in the top view 208B of receiver 204. The top view 208B may also represent the radiograph produced when object 202 is exposed to radiation 206 from radiation source 200 when radiation source 200 is at position 216. The image 212 has a diameter $e_2$. The image 212 produced by the radiation source at position 216 has a greater degree of magnification than the image 210 produced when the source is at position 214. This is due to position 216 being vertically closer to receiver 204 than position 214. Accordingly, the diameter $e_2$ of image 212 is greater than the diameter $e_1$ of image 210. Additionally, as the source is translated to the left from position 214 to position 216, the projected image 212 translates to the right of the position of projected image 210.

The order in which the images 210 and 212 are acquired is not important. For example, image 210 may be acquired after acquiring image 212 by moving the radiation source from position 216 to position 214. Similarly, the distances $d_1$ and $d_2$ may be varied provided that they are known or can be determined using, for example, one or more calibration markers as described herein. The distances $d_1$ and $d_2$ may be selected to ensure acquisition of images of sufficient quality for analysis (e.g., by a doctor and/or computer hardware/software). The distances $d_1$ and $d_2$ may be equal in some embodiments.

It may be observed from FIGS. 2A and 2B that due to magnification, the sizes (diameters) of the images 210 and 212 ($e_1$ and $e_2$ respectively) are greater than the size (diameter) a of the object of interest 202. In order to accurately represent the actual physical size (diameter) a of object 202, the images 210 and 212 may be scaled by the corresponding level of magnification.

Figure 2C:
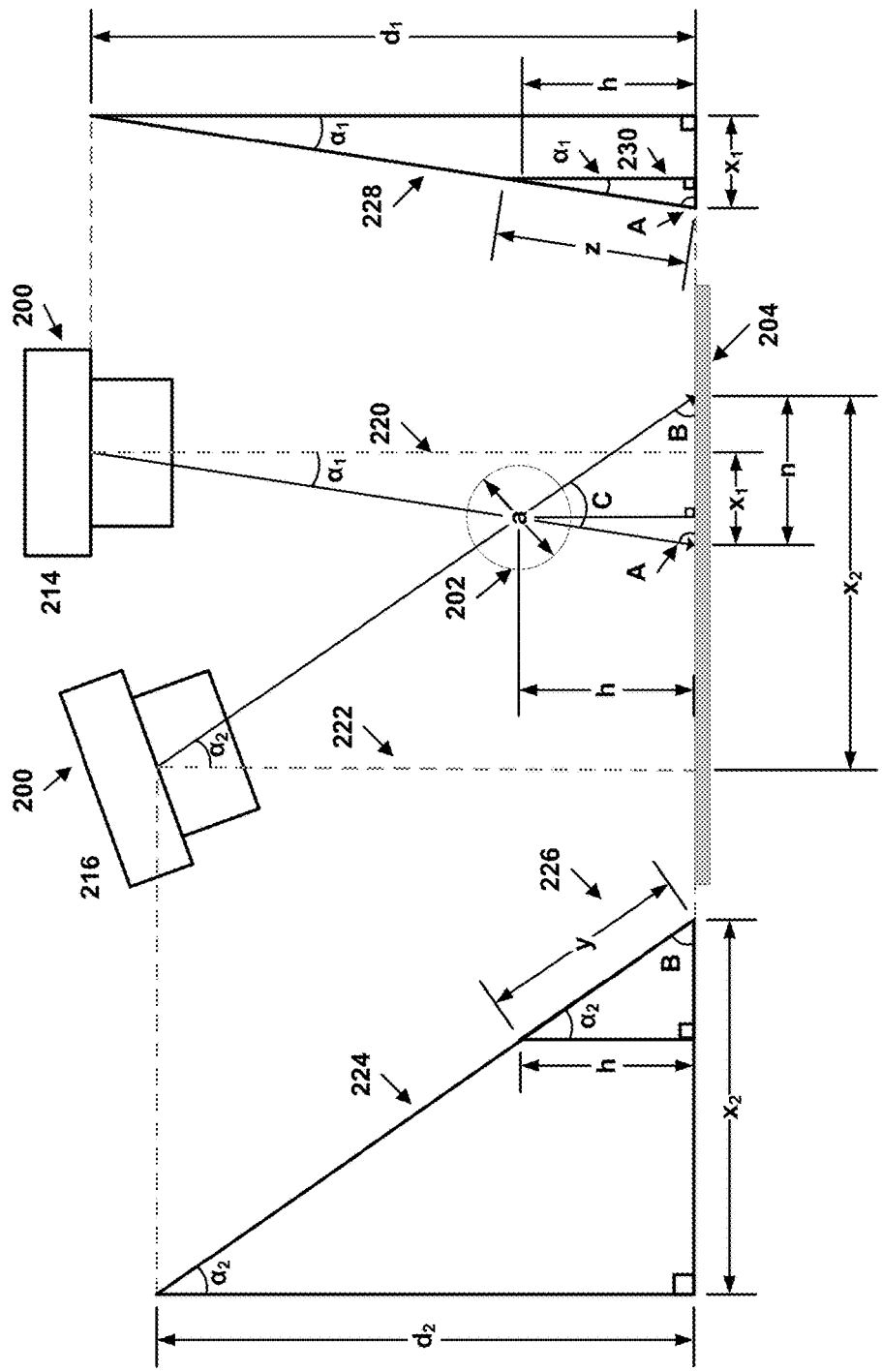
FIGS. 2C and 2D illustrate geometric models of FIGS. 2A and 2B, according to an example embodiment.

FIG. 2C shows an example way of modeling the geometry of the embodiment illustrated in FIGS. 2A and 2B. The size (diameter) a of object 202 is exaggerated to more clearly illustrate the relevant geometry. The level of magnification of images 210 and 212 may be determined to scale at least one of the images by the corresponding level of magnification in order to determine the actual size (diameter) a of object 202.

The length $x_2$ is the horizontal distance (difference in the x-coordinate of position) between the radiation source 200 at position 216 and the center of the corresponding image (the image 212 taken from position 216). The length $x_1$ represents an analogous relationship between the radiation source 200 at position 214 and the corresponding image 210. The horizontal positions 220 and 222 corresponding to radiation source 200 locations 214 and 216, respectively, may be determined from position feedback mechanisms of the radiography system, may be measured/recorded by a radiography technician, and/or may be determined using one or more calibration markers as herein described. The centers of images 210 and 212 may be determined manually, based on user input, or automatically in software using image processing algorithms. For example, when images 210 and 212 are or are expected to be circles or approximately circular, the centers may be found using, for example, the Hough Circle Transform. The distances $x_1$ and $x_2$ may be determined manually, via user input, or automatically, by a computing device executing specialized software, based on the parameters described above.

In the case of a fully automated radiography system, the position (x, y, and z) of the radiation source 200 can be determined in relation to receiver 204 and images 210 and/or 212 based on position feedback associated with radiation source 200 and receiver 204. Alternative embodiments may function with a system without automated position feedback. Specifically, a technician operating the radiation source 200 may keep track of the position of radiation source 200 and may subsequently input the information into hardware or software to associate the coordinates of the radiation source 200 at position 216 with image 212. In further embodiments, the position of the radiation source 200 can be determined in relation to receiver 204 and images 210 and/or 212 based on images of one or more calibration markers contained within the corresponding radiographs, as described herein.

Based on triangle 224 of FIG. 2C, the tangent of the angle B may be expressed by Equation (1), where the distance $d_2$ is the height of radiation source 200 above receiver 204 at position 216.

$$\tan(B) = \frac{d_2}{x_2} \quad (1)$$

Accordingly, angle B may be determined according to Equation (2).

$$B = \tan^{-1}\left(\frac{d_2}{x_2}\right) \quad (2)$$

Similarly, based on triangle 224, the angle $\alpha_2$ may be computed according to Equation (3).

$$\alpha_2 = 90° - B \quad (3)$$

Based on triangle 228 of FIG. 2C, the tangent of angle A may be computed according to Equation (4) where the distance $d_1$ is the height of radiation source 200 above receiver 204 at position 214.

$$\tan(A) = \frac{d_1}{x_1} \quad (4)$$

Accordingly, angle A may be determined according to Equation (5).

$$A = \tan^{-1}\left(\frac{d_1}{x_1}\right) \quad (5)$$

Similarly, based on triangle 228, the angle $\alpha_1$ may be computed according to Equation (6).

$$\alpha_1 = 90° - A \quad (6)$$

Based on triangle 226, of FIG. 2C, the height h of the object of interest 202 may be expressed according to Equation (7).

$$h = (y)\sin(B) \quad (7)$$

Likewise, based on triangle 230, the height of h of the object of interest 202 may be expressed according to Equation (8).

$$h = (z)\sin(A) \quad (8)$$

Figure 2D:
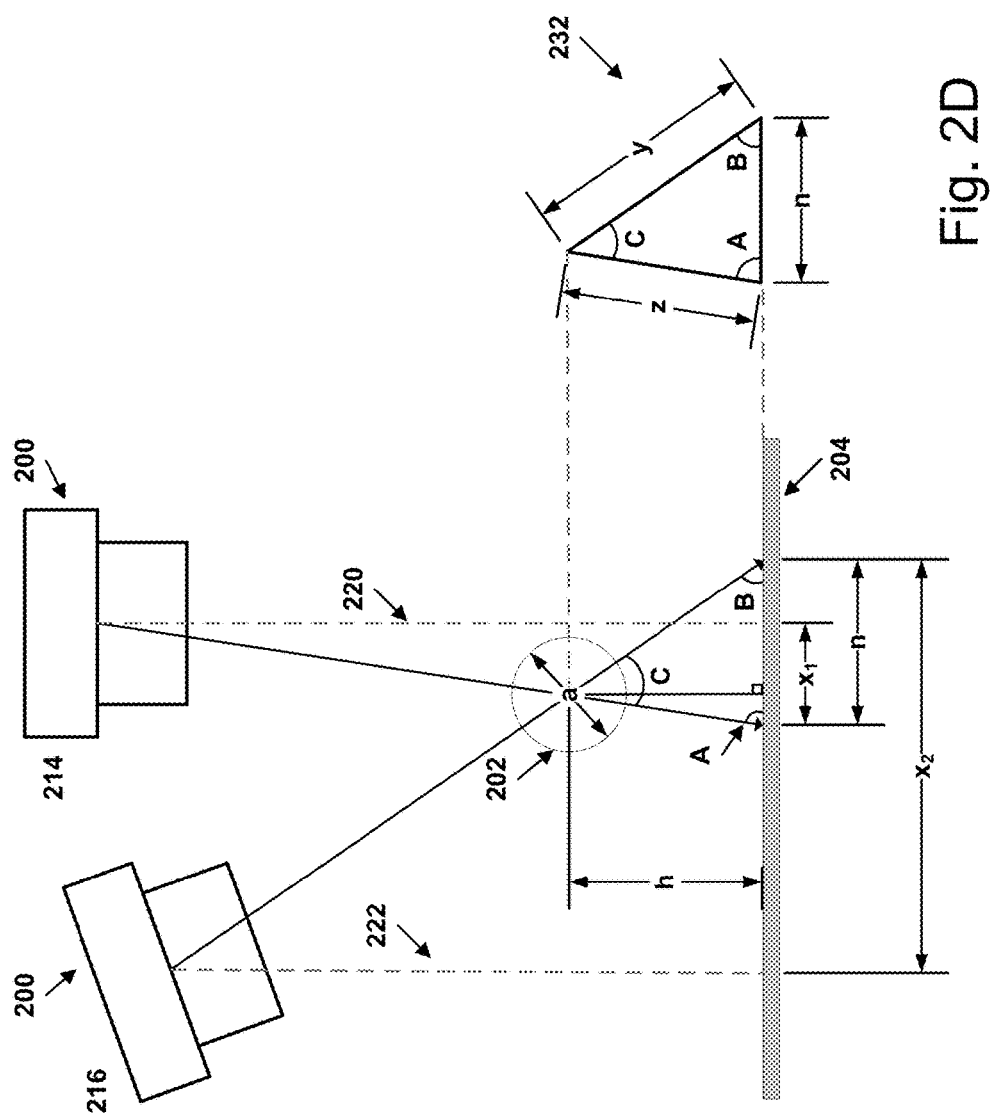

Based on triangle 232 shown in FIG. 2D, hypotenuse y of triangle 226 and hypotenuse z of triangle 230 may be determined using the law of sines according to Equation (9), where n is the distance between the center of image 210 and image 212.

$$\frac{\sin(A)}{y} = \frac{\sin(B)}{z} = \frac{\sin(C)}{n} \quad (9)$$

The distance n is a measurable quantity that may be determined directly from the radiographs using software and/or hardware image processing methods.

Based on FIG. 2C, the angle C may be determined according to Equation (10).

$$C = \alpha_1 + \alpha_2 \quad (10)$$

Accordingly, by combining Equations (2) or (10) with Equation (9), hypotenuse y may be expressed according to Equation (11).

$$y = \frac{(n)\sin(A)}{\sin(C)} \quad (11)$$

Analogously, by combining Equations (5) or (10) with Equation (9), hypotenuse z may be expressed according to Equation (12).

$$z = \frac{(n)\sin(B)}{\sin(C)} \quad (12)$$

Finally, by combining Equations (7) and (11) or Equations (8) and (12), the height h of the object of interest 202 may be determined according to Equation (13).

$$h = \frac{(n)\sin(A)\sin(B)}{\sin(C)} \quad (13)$$

With the height h known, the magnification can be computed for image 210 and/or image 212 according to Equations (14) and (15), respectively. The images may be scaled according to the corresponding level of magnification in order to determine and display the actual physical size (diameter) a of the object of interest 202.

$$M_1 = \frac{d_1}{d_1 - h} \quad (14)$$

$$M_2 = \frac{d_2}{d_2 - h} \quad (15)$$

The determined actual size may be used to select a template closest in shape and size to the object of interest. For example, the object of interest may be a femur or the corresponding acetabulum (femoral socket). The templates may represent a plurality of available replacement femoral stem prosthesis and/or corresponding acetabular prostheses. Selecting a replacement prosthesis closest in size and shape to the actual anatomical size of a patient's femur and acetabulum prior to a hip replacement surgery may ensure that the replacement prosthesis will properly fit the patient's anatomy.

A computing device may be programmed or configured to carry out the operations and/or the embodiments described herein. For example, the computing device may obtain two radiographs or digital representations of the two radiographs (e.g., image files of the radiographs). A first radiograph may contain image 210. The first radiograph may be associated with first metadata indicating the distance $d_1$. Alternatively, the first metadata may contain the spatial coordinates of the radiation source 200 and radiation receiver 204. The distance $d_1$ may be determined from the spatial coordinates using arithmetic operations. In some embodiments, the distance $d_1$ may be determined based on images of one or more calibration markers contained in the first radiograph. Similarly, a second radiograph may contain image 212. Likewise, the second radiograph may be associated with a second metadata indicating, either directly or indirectly, the distance $d_2$. The second radiograph may likewise include images of one or more calibration markers that can be used to determine the distance $d_2$.

The computing device may subsequently scan or search the first radiograph or digital representation thereof to locate the image 210. Similarly, the second radiograph or digital representation thereof may be scanned or searched to locate the image 212. For example, the computing device may be programmed to search for geometric shapes or features such as circles in order to identify the images 210 and 212. Alternatively, a user may identify the images 210 and 212 using a graphical user interface that the computing device is programmed or configured to implement. After locating images 210 and 212 in the respective radiographs, the diameters $e_1$ and $e_2$ of images 210 and 212, respectively, may be determined by, for example, counting the number of pixels along a line that defines the diameter of each circular image 210 and 212.

The computing device may use the determined values of $d_1$, $d_2$, $e_1$, and $e_2$ to implement Equations (1)-(15), as detailed above, in order to determine the magnifications $M_1$ and $M_2$ of images 210 and 212, respectively. The diameters $e_1$ and $e_2$ of images 210 and 212 may be modified according to the corresponding levels of magnification $M_1$ and $M_2$ to represent the actual physical size of object 202. The modification may comprise temporarily adjusting the visual display of the digital representations of images 210 and 212. Alternatively, the modification may comprise permanently storing the adjusted size of images 210 and 212 in a file containing the respective images and/or the corresponding metadata. Other variations are possible. The computing device may also be programmed or configured to perform or interface with a device configured to perform templating and/or digital templating.

IV. Example Operations for Determining Object Spatial Orientation

Figure 3B:
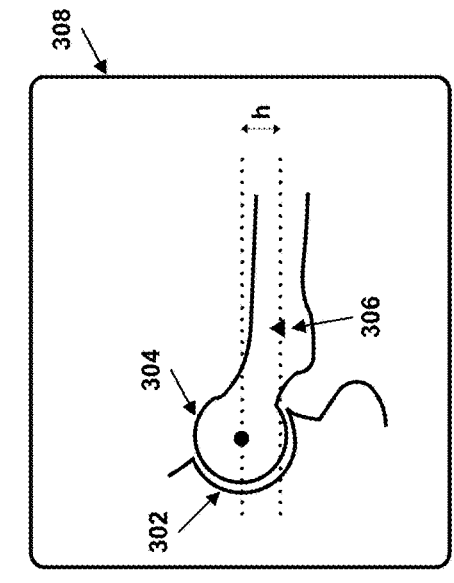
FIG. 3B illustrates a lateral radiograph of the human hip, according to an example embodiment.
Figure 3D:
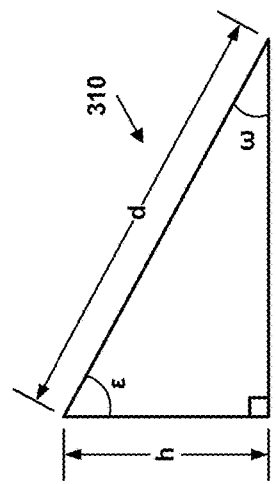
FIG. 3D illustrates a geometric model of the rotated human hip, according to an example embodiment.
Figure 3A:
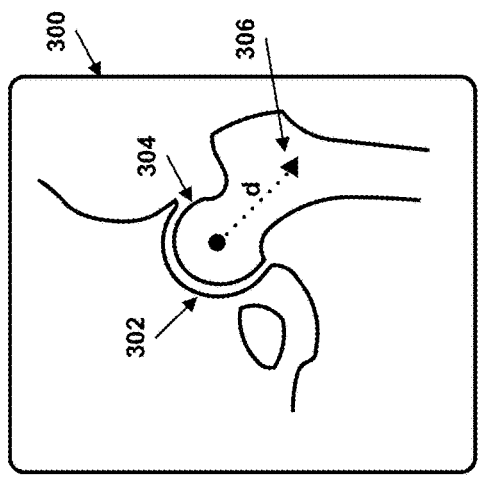
FIG. 3A illustrates an anteroposterior radiograph of a human hip, according to an example embodiment.

FIGS. 3A-3D illustrate an example embodiment enabling the determination of the orientation of an object of interest. Specifically, FIG. 3A illustrates an anteroposterior (AP) radiograph 300 of a human hip. The hip radiograph comprises images of acetabulum 302, femoral head 304, and femoral calcar 306. The center of the acetabulum image 302 and the center of the femoral head image 304 are indicated by a circular marker. The femoral calcar image 306 is indicated by a triangular marker. The two markers are separated by a distance d. The distance d may be determined in the plane of the radiograph 300. A computing device may be programmed or configured to automatically detect the images 302, 304, and 306 and place the markers in the appropriate position. Alternatively, a user may manually place the markers at the appropriate location of the radiograph 300 or a digital representation thereof using a graphical user interface. The computing device may determine the distance d based on the positions of the markers by, for example, counting the number of pixels separating the markers.

FIG. 3B illustrates a cross table lateral hip radiograph 308 of the same human hip. The center of the acetabulum image 302 and the femoral calcar image 306 are located at different heights, separated by a vertical distance h, above the radiographic receiver. In FIG. 3A, the vertical distance h (not illustrated) is coming out of the page. As a result, the femoral calcar image 306 and the acetabulum image 302 have two different magnifications on the AP radiograph 300. A computing device may be programmed or configured to determine the distance h based on the positions of the circular and triangular markers in radiograph 308 as described above.

According to the methods described herein, the image of each object of interest may be scaled based on the level of magnification corresponding to the particular image. For example, the magnification of the acetabulum image 302 may be determined based on the height of the acetabulum above the radiographic receiver, as described with respect to FIGS. 2A-2D. Similarly, the magnification of the femoral calcar image 306 may be determined based on the height of the femoral calcar above the radiographic receiver. For example, radiograph 300 may be a first of two AP hip radiographs. Radiograph 300 may be used with a second AP hip radiograph (not illustrated) according to the embodiments described with respect to FIGS. 2A-2E to determine the magnification of acetabulum image 302 by determining the height of the acetabulum and determine the magnification of the femoral calcar 306 by determining the height of the femoral calcar.

The acetabulum image 302 may be scaled based on its determined magnification to display the actual physical size of the acetabulum. Likewise, femoral calcar image 306 and femoral head image 304 may be scaled based on the determined, corresponding magnifications to display the actual physical size of femoral calcar and femoral head. Accordingly, the templating process may account for the different magnifications of the different anatomical features of the hip. For example, two or more templates may be used, each with a scaling factor accurate for the specific object being measured (e.g. femoral calcar, femoral head, acetabulum). Some embodiments may apply the same scaling factor to every object of interest determined to be at a particular height. Some embodiments may comprise a computing device causing a display to show an object scaled according to its determined magnification, along with an unscaled template overlaid thereon.

Figure 3C:
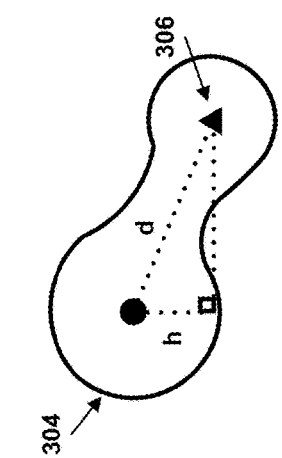
FIG. 3C illustrates an axial view of the human hip, according to an example embodiment.

Additionally, the methods described herein may allow the spatial orientation of an object to be determined based on the height of two or more different points on or features of the object. For example, by determining the height of the femur head corresponding to image 304 and the height of the femoral calcar corresponding to image 306, the rotation of the femur may be determined. FIG. 3C illustrates an axial view (the transverse cross-sectional plane of the human body) of the human hip depicted in radiograph 300 of FIG. 3A and radiograph 308 of FIG. 3B. The overlaid geometry illustrates how the measured distance d and the determined height difference h form a right triangle. The height difference h may be determined by calculating the difference between the height of the femur head and the femoral calcar as previously described. FIG. 3D shows the overlaid geometry of FIG. 3C enlarged and modeled as triangle 310 labeled with the corresponding dimensions. Based on triangle 310, angle ω may be expressed according to Equation (16) and angle E may be expressed according to Equation (17) or, equivalently, according to Equation (18).

$$\omega = \sin^{-1}(h/d) \quad (16)$$

$$\varepsilon = 90 - \omega \quad (17)$$

$$\varepsilon = \cos^{-1}(h/d) \quad (18)$$

In the present example embodiment, the angles ω and ε may represent the extent of hip rotation. For example, angle ω may represent the extent of femoral anteversion. Angle ε may be an alternative way of representing femoral version (twist). Alternative embodiments may determine the spatial orientation of other body parts or objects using the methods described herein. Some embodiments may acquire more than two images in order to determine the spatial orientation in multiple reference planes. Example embodiments may determine the spatial orientation of multiple objects present in the same image. For example, the degree of rotation of both hips may be determined at the same time, provided that the radiograph encompasses both hips.

The determined degree of hip rotation, or more generally, the determined three-dimensional spatial orientation of an object of interest, may be used in combination with templating techniques. Specifically, the object of interest may be templated using templates that reflect the 3D spatial orientation of the object being measured. The templates may be three-dimensional representations of prostheses and may be rotated into that same 3D spatial orientation as the object in order to select a prosthesis closest in size and shape to the object. Alternatively, the templates may be two-dimensional and may comprise a plurality of images of the prostheses representing different spatial orientations of the prostheses.

Figure 4C:
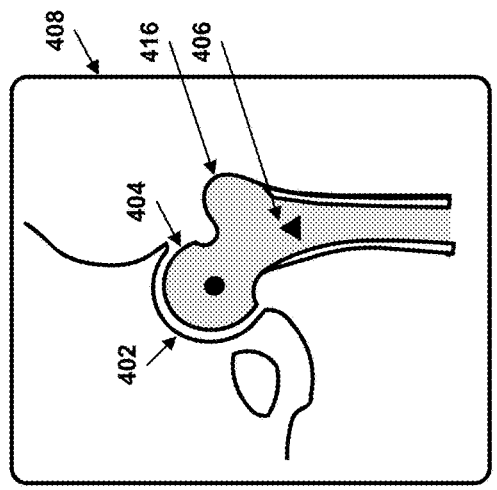
FIG. 4C illustrates an anteroposterior radiograph of the human hip in a rotated position, according to an example embodiment.
Figure 4D:
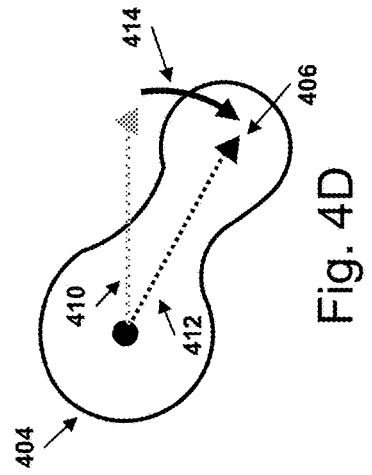
FIG. 4D illustrates an axial view of the human hip in the rotated position of FIG. 4C, according to an example embodiment.
Figure 4A:
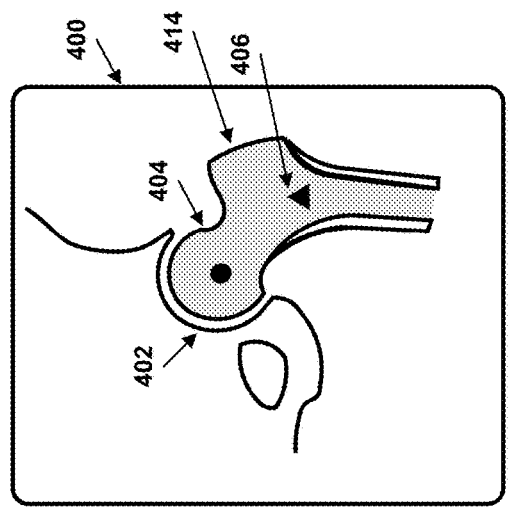
FIG. 4A illustrates an anteroposterior radiograph of a human hip in a neutral position, according to an example embodiment.
Figure 4B:
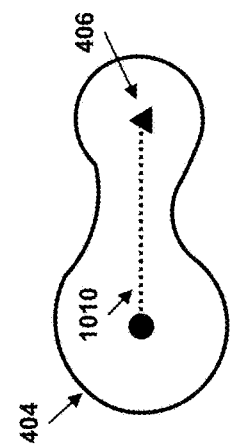
FIG. 4B illustrates an axial view of the human hip in the neutral position of FIG. 4A, according to an example embodiment.

In contrast, using a template that does not correspond to the spatial orientation of the object of interest may result in measurement error because the shape of the image of the object may be significantly different depending on the spatial orienting of the object during image acquisition. For example, the shape of the image of the hip changes significantly as the hip is rotated, as illustrated in FIGS. 4A-4D. FIG. 4A illustrates a radiograph 400 of a human hip comprising acetabulum image 402, femoral head image 404, and femoral calcar image 406. The radiograph 400 is taken when the hip is at a neutral position as illustrated by the axial view of the hip in FIG. 4B. Specifically, the line 410, connecting the circular marker indicating the center of the head of the femur and the triangle indicating the femoral calcar, is horizontal (parallel to the coronal plane of the human body). FIG. 4C illustrates a second radiograph 408 of the same human hip taken when the hip is rotated. The degree of rotation is illustrated in FIG. 4D by line 414, showing the change from the original alignment of the circular marker indicating the center of the head of the femur and the triangle indicating the femoral calcar along line 410 to the new alignment along line 412. It may be observed that the anatomical feature image 414 of the femur in radiograph 400 looks different than anatomical feature image 416 in radiograph 408 due to the femur being oriented (rotated) differently in the two images.

Consequently, using a template that does not reflect the same degree of rotation as does the image of the hip may result in selection of a hip replacement prosthesis that does not accurately match the anatomy of a given patient. Determining the degree of hip rotation, as described above, allows for the selection of a template that corresponds to the image of the hip at the given orientation. As a result, the process of selecting a replacement hip prosthesis may be based on templates that accurately reflect the orientation of the hip at the time of image acquisition. Furthermore, the advantages of rotational template adjustment, as described above, are not limited to hip and may be extended to any body part of interest. The techniques described herein may also be applied during radiographic imaging without the templating process in order to produce a more accurate representation of the anatomical proportions of the objects of interest.

V. Example Implementations Using A Calibration Marker

Existing approaches for determining image magnification require that a medical professional (e.g., a radiography technician) place a marker of known size at the same height as the object of interest. Such methods rely on only one image of the object of interest. Since the marker and the object of interest are at the same height, the magnification of the object of interest should be the same as the magnification of the marker. Additionally, since the size of the marker is known, the magnification may be determined based on the ratio of the size of the image to the actual size of the marker.

This method assumes that the marker was correctly placed at the height of the object of interest, using proper technique by the medical professional. When the marker is not placed correctly, the size of the object of interest may be incorrectly determined, leading to complications. For example, in the case where the hip is being sized for a replacement prosthesis, determining the size incorrectly may lead to the medical professional ordering incorrectly sized hardware and/or attempting to insert the incorrectly sized hardware during surgery. The embodiments described herein eliminate the need for positioning a calibration marker at the same height as the object of interest. The embodiments described herein further eliminate the need for attaching the markers to the patient and/or referencing anatomical features of the patient in placing the calibration markers.

In automated radiography systems, human error associated with positioning the radiation source and receiver is eliminated. The embodiments described herein may accurately determine the size and orientation of the object of interest based an accurate record of the relative position between a radiation source and a radiation receiver at the moment that a corresponding radiograph is captured. However, in radiography systems without automated position feedback systems, a technician may manually determine and record the relative position of the radiation source and the receiver. Human error in positioning the radiation source and receiver, determining the relative position between the radiation source and receiver, and/or recording the relative position between the radiation source and receiver may result in errors in the determined image magnification which may in turn lead to surgical complications.

The example embodiments that follow, in combination with the operations described above, may allow for the reduction or elimination of human error by using one or more calibration markers to determine the relative position of the radiation source and the radiation receiver. Contrary to other methods, the calibration markers may not need to be placed at the same height as the object of interest. Instead, the marker may be attached to the radiation source or placed on the radiation receiver or radiation receiver holder (e.g., patient table). The markers may be removably attached to the radiation source, the radiation receiver, or another component of the radiographic imaging system using the calibration marker positioning stands herein described. The calibration marker approach described herein does not require additional staff training and/or testing and may be used with any radiation imaging apparatus.

In general, the calibration marker method may be used whenever consistent placement of the radiation source in relation to the radiation receiver is important. The marker itself may be made of any material such that, under commonly used radiation intensities and exposure times, a clear image of the marker is produced on the radiation receiver (otherwise called a radio-dense material). In some embodiments, two or more calibration markers may be used. Each marker may have a different radio-density. The radio-density of a respective calibration marker of the two or more calibration markers may correspond to intensity of an image of the respective marker produced on a radiation receiver (e.g., a radiograph) of the radiographic imaging device.

The one or more calibration markers may be used to identify and correct for errors in the placement of the radiation source and other human error. Specifically, the calibration marker method may be used to accurately determine the position of the radiation source relative to the radiation receiver in systems where that position is not automatically determined or where manual determination of the position may be subject to errors. Alternatively or additionally, the calibration marker may be used to determine the difference between the known height of the calibration marker and an unknown height of the object of interest.

In general, the marker may have a known size and may be positioned at a known position, vertical and/or horizontal, in relation to either the source or receiver. Mathematically, the number of known variables with respect to the size and/or position of the calibration marker may be equal to or greater than the number of independent equations describing the position of the radiation source in relation to the receiver in a particular geometric arrangement. As a result, the position of the radiation source in relation to the receiver may be determined based on the known properties of one or more calibration markers.

Figure 5A:
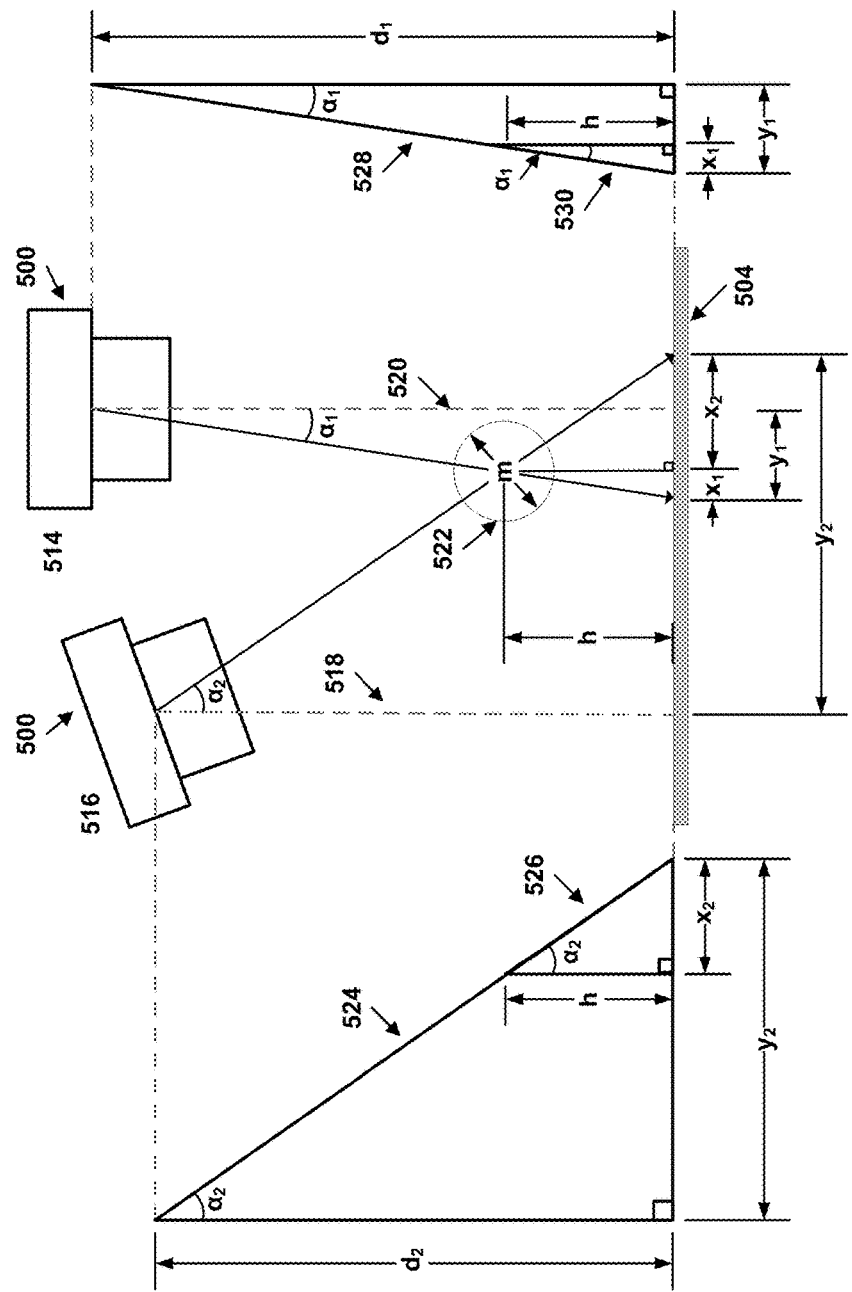
FIG. 5A illustrates an example of a calibration marker being used to determine the position of a radiation source, according to an example embodiment.

FIG. 5A illustrates an example embodiment in which a calibration marker is used to determine the height of the radiation source. Similarly to FIGS. 2A-2D, two images of the calibration marker 522 and the object of interest (not shown) may be taken using radiation source 500 positioned above receiver 504. The first image may be taken with radiation source 500 at position 514, an unknown distance $d_1$ above the receiver 504. The horizontal position, designated by line 520, may also be unknown. Similarly, a second image may be taken with radiation source 500 at position 516, an unknown distance $d_2$ above the receiver 504. The horizontal position, designated by line 518, may also be unknown. The position of the radiation source 500 in relation to the radiation receiver 504 may be unknown due to a lack of means for measuring the distance accurately, uncertainty in measurements of the position, and/or erroneous measurements of the position by a radiography technician. The calibration marker may be used to determine, verify, and/or validate the position of the radiation source 500 in relation to receiver 504. The calibration marker 522 may have a known size m, a known height h, and may be placed at a known horizontal distance in relation to the radiation receiver 1204.

The distance $d_1$ may be determined based on the magnification of the marker of known size m. Specifically, $d_1$ may be derived from Equation (19), where ($e_1$) is the size of the first image (image taken from position 514, not shown).

$$M_1 = \frac{d_1}{d_1 - h} = \frac{e_1}{m} \qquad (19)$$

The distance $d_1$ may be expressed according to Equation (20).

$$d_1 = \frac{e_1 h}{e_1 - m} \qquad (20)$$

Likewise, $d_2$ may be derived from Equation (21), where $e_2$ is the size of the second image (image taken from position 516, not shown).

$$M_2 = \frac{d_2}{d_2 - h} = \frac{e_2}{m} \qquad (21)$$

The distance $d_2$ may be expressed according to Equation (22).

$$d_2 = \frac{e_2 h}{e_2 - m} \quad (22)$$

The horizontal position of the radiation source 500 at position 514 may be derived based on triangles 528 and 530. Specifically, the angle $\alpha_1$ may be expressed according to Equation (23), where $x_1$ is the distance between the center of the image taken from position 514 and the x-position of the calibration marker 522.

$$\alpha_1 = \tan^{-1}\left(\frac{x_1}{h}\right) \quad (23)$$

The distance $y_1$ corresponding to the distance between the center of the first image taken from position 514 and the x-position of the radiation source 500 at position 514 may be expressed according to Equation (24).

$$y_1 = d_1 \tan(\alpha_1) \quad (24)$$

Consequently, the spatial position of radiation source 500 in relation to receiver 504 may be determined based on known properties of the calibration marker. The analogous procedure may be carried out for triangles 524 and 526 to determine the distance $y_2$ according to Equation (25).

$$y_2 = d_2 \tan(\alpha_2) \quad (25)$$

With the spatial position of the radiation source 500 in relation to receiver 504 known at both positions 514 and 516, the magnification of the image of the object of interest (not shown) may be determined. The determined magnification may be used to scale the image of the object of interest in order to determine the actual physical size of the object of interest. The scaled image of the object of interest may subsequently be used with digital templating methods to determine a template closest in size to the actual physical size of the object of interest.

In some example embodiments, the calibration marker may be disposed upon or connected to a radiation receiver housing, instead of being placed directly on the radiation receiver itself. Alternatively, the calibration marker may be placed on or connected to a radiographic table next to or above the radiation receiver housing. In some example embodiments, the radiation receiver housing may have a feature, structure, or mechanism on or in which a calibration marker may be placed or attached. For example, some radiation systems may comprise a radiation receiver in the form of an X-ray cassette. The X-ray cassette may be held by or housed in a cassette holder. The calibration marker may be placed on the cassette holder. However, in some radiography systems, the radiation receiver might fit imprecisely in the radiation receiver housing. For example, the radiation receiver housing may be slightly bigger than the radiation receiver (e.g., the cassette holder may be bigger than the X-ray cassette). The imprecise fit may allow the radiation receiver to move around inside the radiation receiver housing. Consequently, since the calibration marker may be placed on the radiation receiver housing or on a radiographic table, the position of the calibration marker in relation to the radiation receiver may undesirably change between acquisitions of the first radiograph and the second radiograph.

For example, a first radiograph may be captured on a first X-ray cassette held in a cassette holder. The first X-ray cassette may be removed from the cassette holder. The radiation source may be moved to a second position and/or orientation with respect to the X-ray cassette and/or the cassette holder. A second X-ray cassette may be inserted into the cassette holder. However, due to an imprecise fit, the second cassette may be in a slightly different position inside the cassette holder than the first X-ray cassette. While the calibration marker may remain in the same position in relation to the radiation receiver housing, the calibration marker may be in a slightly different position in relation to the radiation receiver itself (the second X-ray cassette). Accordingly, calculations that assume that the calibration marker is in the same position in relation to the first radiation receiver (first X-ray cassette) and the second radiation receiver (second X-ray cassette) may produce results containing calculation errors.

In some embodiments, the radiation receiver may be an integral part of the radiation receiver housing. For example, in radiography systems where the radiation receiver is an electronic detector (e.g., sensor array), the radiation receiver might not need to be changed between acquisitions of successive images. In such embodiments, placement of the calibration marker on the radiation receiver housing, positioning of the calibration marker with respect to the radiation receiver housing, and/or attachment of the calibration marker to the radiation receiver housing may be equivalent to placement, positioning, and/or attachment of the calibration marker to the radiation receiver itself since the radiation receiver and the radiation receiver housing may be precisely and firmly fitted and/or connected together. Alternatively, the calibration marker may be placed, positioned, and/or attached directly to the radiation receiver itself as opposed to the radiation receiver housing. For example, the calibration marker may be placed, positioned, and/or attached directly to the electronic detector as opposed to the housing of the detector. In embodiments utilizing X-ray film and/or X-ray cassettes, placement, positioning, and/or attachment of the calibration marker directly to the film or cassette may be impossible, impractical, or inaccurate. Accordingly, FIG. 5B illustrates an example embodiment that may be used to account for an imprecise fit of a radiation receiver inside of a radiation receiver housing.

Figure 5B:
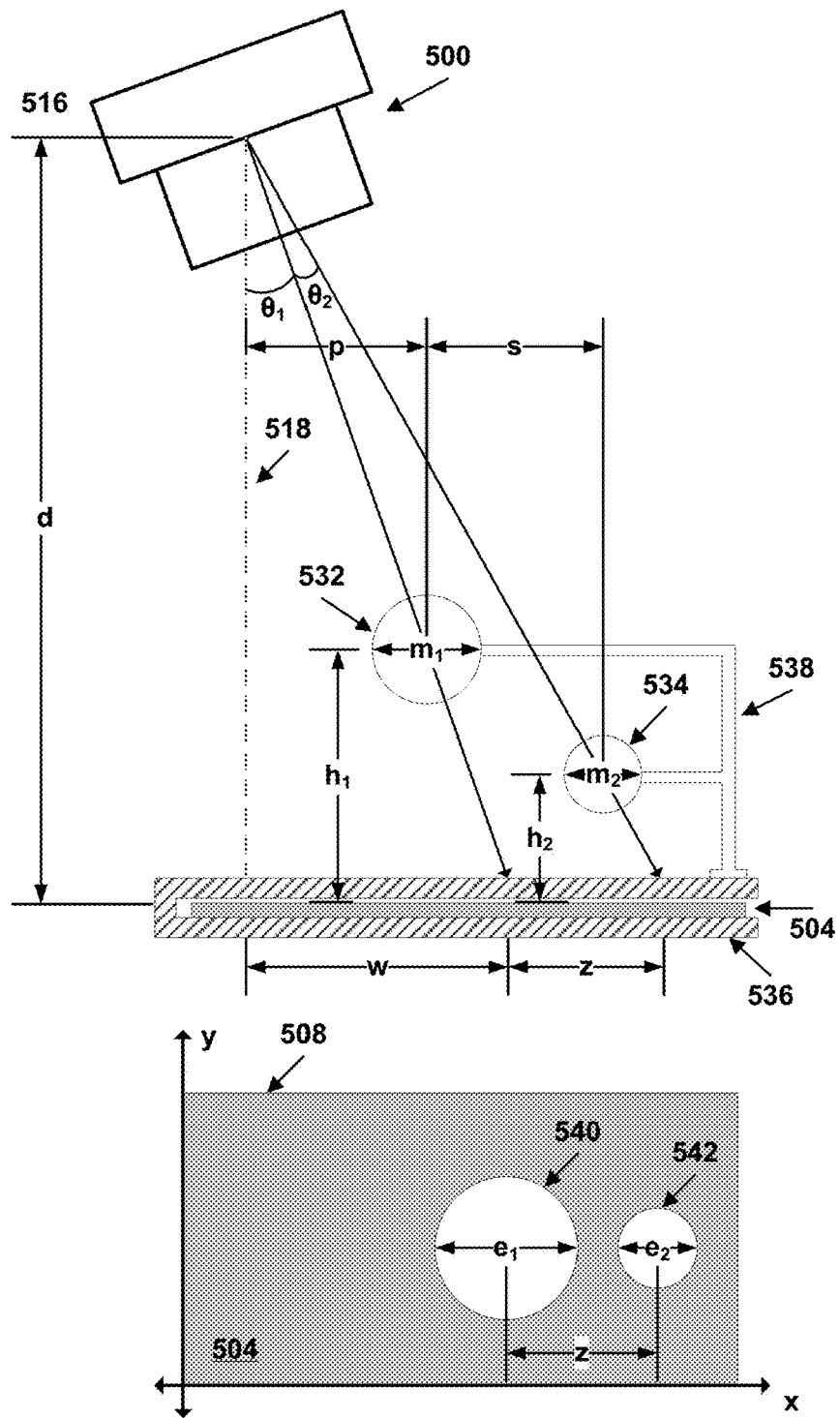
FIG. 5B illustrates another example of a calibration marker being used to determine the position of a radiation source, according to an example embodiment.

In particular, FIG. 5B illustrates a radiation source 500 located at position 516 above radiation receiver 504. Position 516 may be a distance d above the radiation receiver 504 and may correspond to an x-coordinate position represented by line 518. Radiation receiver 504 may be housed in a radiation receiver housing 536. The radiation receiver 536 may also be called a radiation receiver holder (e.g., X-ray cassette holder). The radiation receiver 504 may be smaller than radiation receiver housing 536, resulting in an imprecise fit of the radiation receiver 504 in the radiation receiver housing 536. Accordingly, there may be variation in how different radiography technicians or medical professionals position the radiation receiver 504 in radiation receiver housing 536.

FIG. 5B additionally illustrates a first calibration marker 532 and a second calibration marker 534 attached to or retained by a calibration marker support structure 538. The calibration marker support structure 538 may be placed on, positioned with respect to, and/or attached to the radiation receiver housing 536 at a known position. For example, radiation receiver housing 536 may have a special slot specifically designed to retain and/or attach to the calibration marker support structure 538. However, this is not required.

Additionally, described herein are devices and mechanisms for positioning and retaining one or more calibration markers with respect to a radiographic imaging device during capturing of radiographic images.

The first calibration marker 532 may have a known diameter $m_1$ and may be located at a known height $h_1$ above the radiation receiver. The second calibration marker 534 may also have a known diameter $m_2$ and may be located at a known height $h_2$ above the radiation receiver. The calibration markers 532 and 534 may be separated from each other by a known horizontal distance s. The calibration markers 532 and 534 may produce corresponding images 540 and 542, respectively, as illustrated in the top view 508 of radiation receiver 504.

An x-y coordinate frame is shown attached to the top view 508 of radiation receiver 504. Variation in positioning of the radiation receiver 504 inside of the radiation receiver housing 536 may include a variation in the y-coordinate position of the radiation receiver 504 and/or a variation in the x-coordinate position of the radiation receiver 504. Since the calibration markers 532 and 534 are located in a known position with respect to the radiation receiver housing 538, variation in the position of the radiation receiver 504 inside the radiation receiver housing 536 may change the relative position between the radiation receiver 504 and the calibration markers 532 and 534. Under such conditions, an assumption or estimation of the location of the calibration markers 532 and 534 in relation to the radiation receiver 504 may be inaccurate and/or incorrect and may lead to an inaccurate determination of the magnification of the corresponding images of an object of interest.

However, by using at least two calibration markers, as illustrated in FIG. 5B, the position of the radiation source 500 in relation to the radiation receiver 504 may be determined without assuming or estimating the position of the at least two calibration markers in relation to the radiation source 504. Instead, determination of the position of the radiation source 500 in relation to the radiation receiver 504 may be based on the known distance s between the two calibration markers. Specifically, the height d of the radiation source 500 above radiation receiver 504 may be determined using either calibration marker 532 and image 540 or calibration marker 534 and image 542. Alternatively, some embodiments may perform a redundant calculation using both calibration markers 532 and 534 and corresponding images 540 and 542 in order to verify the results against each other.

Figure 5C:
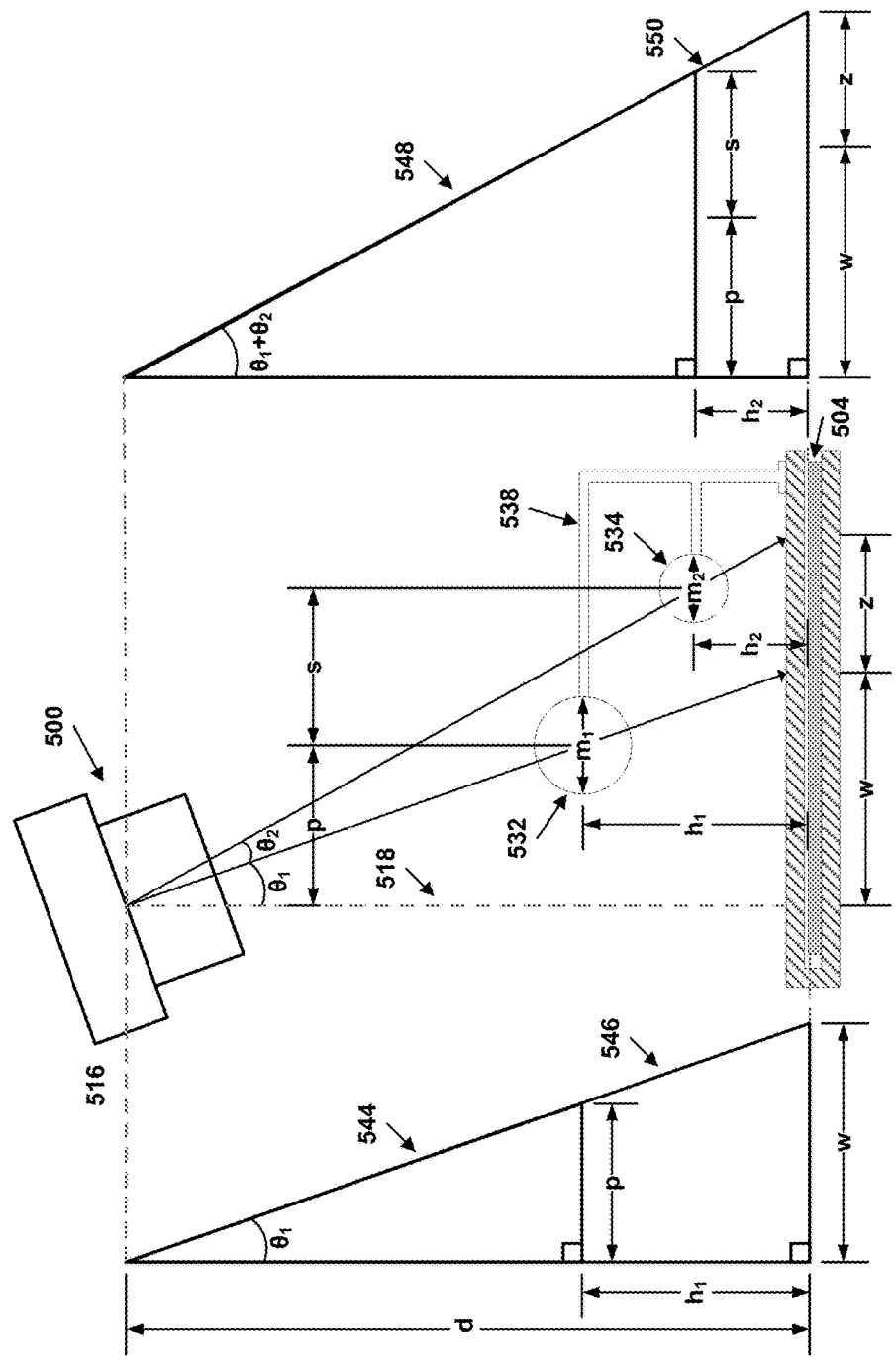
FIG. 5C illustrates a geometric model of FIG. 5B, according to an example embodiment.

The embodiment illustrated in FIG. 5B may be modeled as illustrated in FIG. 5C. The example model illustrated in FIG. 5C may be used to determine the position of radiation source 500 in relation to radiation receiver 504 and avoid any error resulting from imprecise positioning of the radiation receiver 504 inside radiation receiver housing 536. In particular, Equations (26) and (27) may be written based on triangles 544 and 546, respectively.

$$\tan(\theta_1) = \frac{p}{d - h_1} \qquad (26)$$

$$\tan(\theta_1) = \frac{w}{d} \qquad (27)$$

The distance z may be determined based on a radiograph containing the images 540 and 542 by measuring the distances between the centers of the respective images. Alternative embodiments may utilize a geometric model where the distance z may be determined between the edges of images 540 and 542. In some embodiments, the distance z may be determined by a computing device using known feature detection and image recognition algorithms such as, for example, the Hough circle transform. Equations (26) and (27) may be combined into Equation (28).

$$\frac{p}{d - h_1} = \frac{w}{d} \qquad (28)$$

Similarly, Equations (29) and (30) may be written based on triangles 548 and 550, respectively, where distance p is the distance between calibration marker 532 and the line 518 representing the x-coordinate of the radiation source 500.

$$\tan(\theta_1 + \theta_2) = \frac{p + s}{d - h_2} \qquad (29)$$

$$\tan(\theta_1 + \theta_2) = \frac{w + z}{d} \qquad (30)$$

Equations (29) and (30) may be combined into Equation (31).

$$\frac{p + s}{d - h_2} = \frac{w + z}{d} \qquad (31)$$

Equations (28) and (31) may be combined and used to determine the distance w according to Equation (32).

$$w = \frac{z(d - h_2) - sd}{h_2 - h_1} \qquad (32)$$

After determining d and w for the first orientation, a second radiograph may be acquired from a second orientation by changing the relative position between the radiation source 500 and the radiation receiver 504. The position of the radiation source 500 in relation to radiation receiver 504 in the second orientation may be determined in an analogous manner. The determined positions of the radiation source 500 in relation to the radiation receiver 504 in the two orientations may be used to determine a magnification of an image of an object of interest (not shown) by determining the height of the object of interest above the radiation receiver 504 according to any of the embodiments described herein. For example, the magnification may be determined by measuring a size (e.g., dimension such as a diameter, width, length, etc.) of an image of an object of interest as discussed in detail with respect to FIGS. 2A-2D. Alternatively, the magnification may be determined by measuring a distance between an anchor point and a reference point on the image of the object of interest, as discussed in detail with respect to FIGS. 6C-6E.

Figures 6A, 6B:
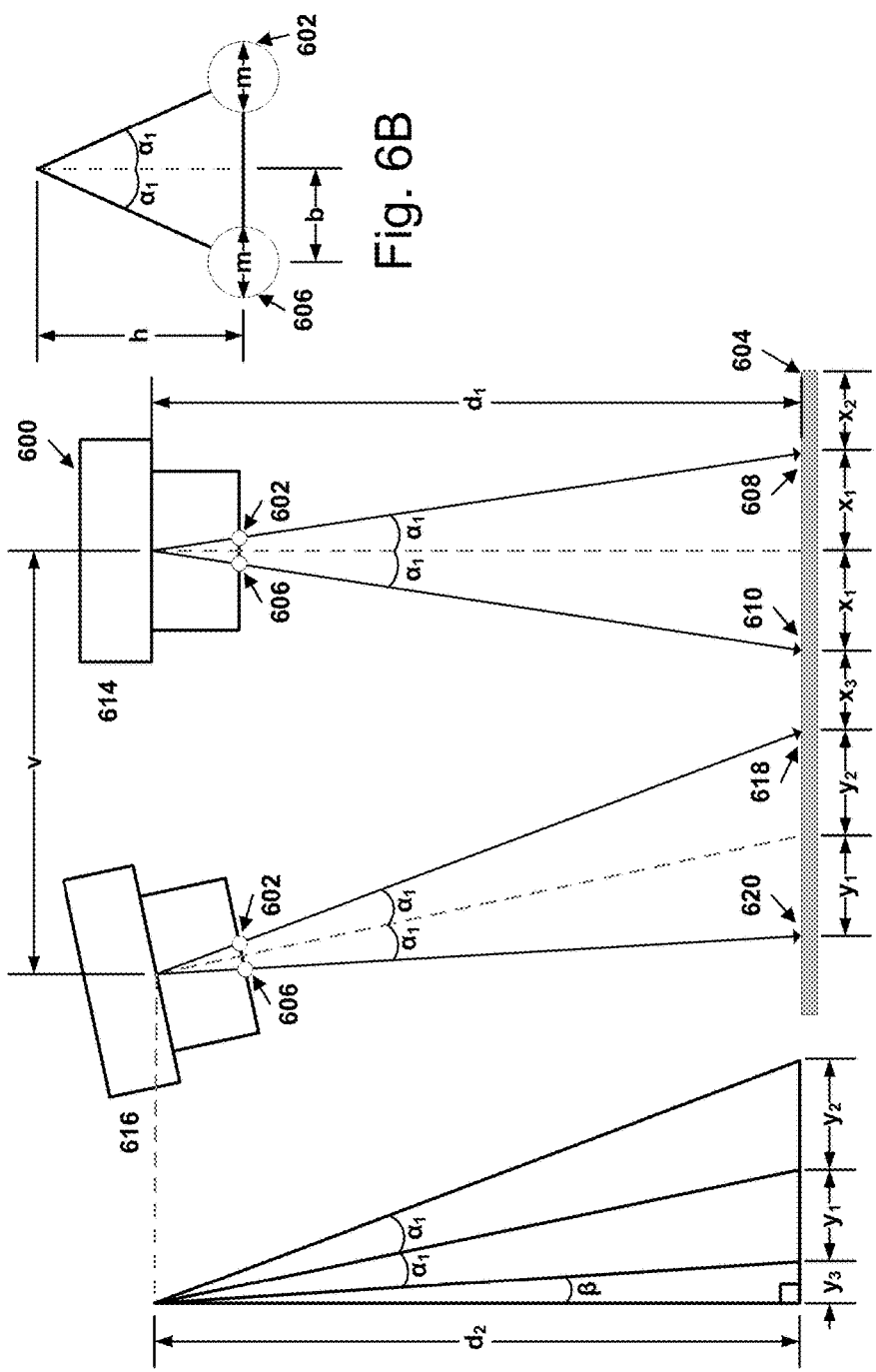
FIGS. 6A and 6B illustrate a calibration marker attached to a radiation source, according to an example embodiment.

FIG. 6A illustrates an embodiment where a calibration marker may be attached to a radiation source or radiation source housing. The calibration marker may be used to correct for errors in radiographic technique by solving for the exact position of the radiation source relative to a radiation receiver. Radiation source 600 is positioned at location 614 above a radiation receiver 604. The radiation beam projected by radiation source 600 may be adjusted, automatically or manually, to a position directly perpendicular to radiation receiver 604. Two calibration markers 602 and 606 are attached to the radiation source 600. FIG. 6B illustrates a scaled geometric representation of the region surrounding the calibration markers 602 and 606. Specifically, FIG. 6B illustrates that both markers have a size m and are offset by a known height h and a known horizontal distance b from the radiation beam. The marker 602 produces image 608 having a size $e_1$ (not shown) and marker 606 produces image 610 also having a size $e_1$ (also not shown). The radiation source 600 at position 614 is an unknown distance $d_1$ above the radiation receiver. The distance $d_1$ may be unknown or uncertain for any of the reasons previously described herein.

The calibration markers 602 and 606 may be used to determine the distance $d_1$. Specifically, $d_1$ may be determined based on the trigonometric relations of Equations (33) and (34).

$$\tan(\alpha_1) = \frac{b}{h} \tag{33}$$

$$\tan(\alpha_1) = \frac{x_1}{d_1} \tag{34}$$

Using these equations, the distance $d_1$ may be expressed according to Equation (35), where h and b are known and $x_1$ may be determined based on the images 608 and 610.

$$d_1 = \frac{x_1 h}{b} \tag{35}$$

For example, an image representation of the entire radiation receiver 604, including images 608 and 610, may be digitized and processed in software to measure the distances $x_1$, $x_2$, and $x_3$ using known image processing methods. Since the distance $x_1$ and the position $x_2$ of image 608 relative to the radiation receiver 604 are known, the relative position $x_1+x_2$ between the radiation source 600 and the radiation receiver 604 is also known.

The distance $d_1$ may alternatively be determined based on the magnification of images 608 and 610. Specifically, the magnification $M_1$ of image 608 may be expressed according to Equation (36). Accordingly, the distance $d_1$ may be expressed according to Equation (37).

$$M_1 = \frac{d_1}{h} = \frac{e_1}{a} \tag{36}$$

$$d_1 = \frac{e_1 h}{a} \tag{37}$$

Some embodiments may carry out both calculations. Since both embodiments are expected to provide the same result, the redundant calculations may serve as a safety net to catch errors. Although not illustrated, an image of an object of interest may also be acquired at the same time as images 608 and 610 are acquired. Consequently, the determined position of radiation source 600 in relation to radiation receiver 604 may be used to determine the magnification or orientation of the object of interest via any of the embodiments described herein.

The radiation source 600, radiation receiver 604, and the calibration markers 602 and 606 may be configured such that images produced by the calibration markers 602 and 606 do not significantly overlap the image of the object of interest. Alternatively, the images of the calibration marker may be acquired during a first exposure of the calibration markers 602 and 606 to radiation from radiation source 600. After the first exposure, the calibration marker may be moved out of the radiation field or removed from the radiation source 600 entirely. The object of interest may subsequently be placed between the radiation source 600 and the radiation receiver 604 without changing the relative position of the radiation source 600 and the radiation receiver 604. The image of the object of interest may be acquired during a second exposure.

The radiation source 600 may subsequently be translated from position 614 to position 616 by a distance v. The marker 602 may now produce an image 618 and marker 606 may produce image 620, separated from each other and from images 608 and 610 by distances $y_1$, $y_2$, and $x_3$ as shown in FIG. 6A. In a first embodiment, the distance v may be accurately determined via direct measurement. For example, the radiation source 600 may include a ruler that can accurately track the horizontal position of radiation source 600. Additionally, the vertical position of the radiation source 600 may remain unchanged, resulting in the distance $d_2$ being equal to the distance $d_1$. Consequently, the relative position between the radiation source 600 and radiation receiver 604 may be determined via arithmetic. Specifically, with the relative position $x_1+x_2$ between the radiation source 600 and receiver 604 at position 614 already known, the horizontal position of location 616 may be determined by adding the distance v to the horizontal coordinate of position 614 and may be expressed as $x_1+x_2+v$.

In a second embodiment, the distance v may be known but the distance $d_2$ may have changed; the distance $d_2$ may be different from the distance $d_1$. Accordingly, the distance $d_2$ may be determined based on the magnification of image 618 of marker 602 or the magnification of image 620 of marker 606 as previously described. Alternatively, the distance may be computed based on the trigonometric relation of Equation (38) and may be expressed according to Equation (39).

$$\tan(\beta + 2\alpha_1) = \frac{v - x_1 - x_3}{d_2} \tag{38}$$

$$d_2 = \frac{v - x_1 - x_3}{\tan(\beta + 2\alpha_1)} \tag{39}$$

In a third embodiment, distances $d_2$ and v may both be unknown. The distance $d_2$ may be determined based on the magnification of the image of either marker 602 or 606 as previously discussed. The distance v may be expressed by Equation (40), where $y_3$ is the only unknown quantity while all other variables can be determined explicitly based on the images 608, 610, 618, and 620 or as previously described herein.

$$v = y_3 + y_1 + y_2 + x_3 + x_1 \tag{40}$$

Accordingly, $y_3$ may be derived from Equation (41) and expressed according to Equation (42).

$$\tan(\beta + 2\alpha_1) = \frac{y_3 + y_1 + y_2}{d_2} \tag{41}$$

$$y_3 = d_2 \tan(\beta + {}^2\alpha_1) - y_1 - y_2 \tag{42}$$

Similarly to prior embodiments, the distance v may now be computed explicitly and added to the x-position of the radiation source 600 at location 614 to determine the x-position of the radiation source 600 at location 616 in relation to radiation receiver 604. The now known relative position may be used by any of the methods described herein to determine the magnification and orientation of an object of interest. The image of the object of interest may be scaled and used in digital templating methods to determine a template object closest in size to the object of interest.

In general, more or fewer calibration markers may be used. For example, some embodiments may use three calibration markers attached to the radiation source 600. Regardless of their number, the calibration makers may be arranged in a particular pattern that facilitates identification of the image corresponding to each calibration marker in a radiograph. Alternatively or additionally, the calibration markers may be arranged in a way that simplifies the computation and/or calculations involved in determining the relative position between radiation source 600 and radiation receiver 604. Some embodiments may use both calibration markers attached to the radiation source 600 as well as calibration markers attached to the radiation receiver 604.

Alternative embodiments may use multiple redundant calibration markers in order to reduce or eliminate errors by verifying and/or double-checking any calculations. An example embodiment may have a calibration marker attached in a known position relative to the radiation source 600 and may determine the position of radiation source 600 in relation to radiation receiver 604 based on the image of the calibration marker in the corresponding radiograph. A second calibration marker may be attached in a known position relative to the radiation receiver 604. The image of the second calibration marker may also be used to determine the position of radiation source 600 in relation to radiation receiver 604 based on the image of the second calibration marker in the corresponding radiograph. When the two calculations produce significantly different results, a medical professional and/or computing device may require or suggest that the radiographs be taken again in a more careful manner. Conversely, when the calculations produce the same result, the medical professional may be confident in the accuracy of the procedure.

Figure 6E:
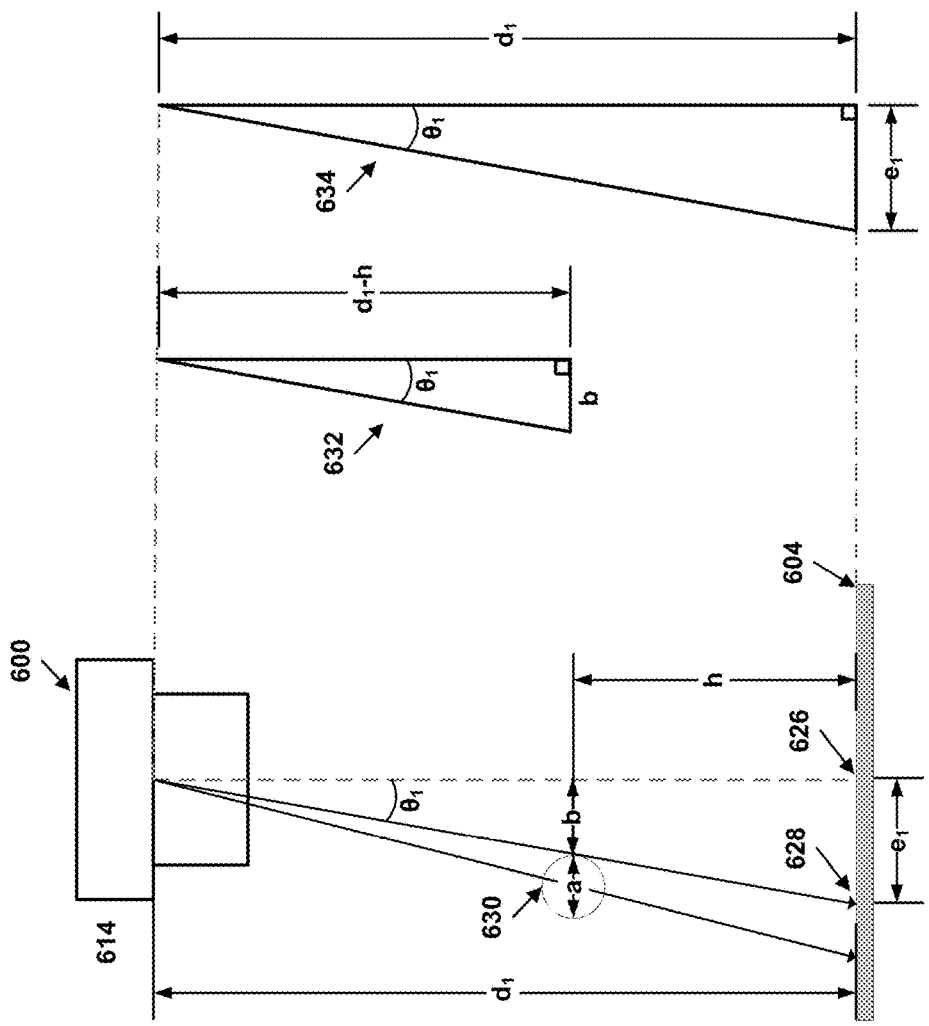

FIGS. 6C-6E illustrate an exemplary embodiment where a magnification of an object of interest is determined based on measurements of a distance between a reference point in an image of the object of interest and an anchor point (another reference point). Specifically, the magnification is based on a first distance between a first reference point of an image of the object of interest contained in a first radiograph and an anchor point in the first radiograph and further based on a second distance between the first reference point of an image of the object of interest contained in a second radiograph and the anchor point in the second radiograph. The anchor point may be another reference point but is referred to herein as an anchor point in order to differentiate it from a reference point in an image of the object of interest. The distinction will be made clear by way of the following example.

FIG. 6C illustrates a radiation source 600 positioned at position 614, a distance $d_1$ above a radiation receiver 604. Two calibration markers, 602 and 606, may be attached to the radiation source 600. The calibration markers 602 and 606 may create corresponding calibration markers images 608 and 610. As shown in FIG. 6D, the images 608 and 610 (shown surrounded by dotted circles for emphasis) may be contained in radiograph 622 acquired using radiation source 600 at position 614 in relation to radiation receiver 604. A computing device may locate images 608 and 610 in the representation of radiograph 622 by, for example, comparing the color and/or brightness of the pixels in the representation. For circular images, the computing device may look for groups of pixels that fit a model of a circle using the Hough Circle Transform algorithm. The images may 608 and 610 may be separated by a distance $2x_1$. Line 624 connecting the images 608 and 610 may be determined. A midpoint 626 of the line may be determined and may subsequently be used as an anchor point in determining the magnification of the object of interest, according to the present example embodiment.

A distance $e_1$ may be determined or measured between center point (anchor point) 626 and a reference point 628 on the image 627 of the object of interest. The object of interest may be a femoral calcar, as shown in FIG. 6D. In some embodiments, the object of interest may be another anatomical feature. FIG. 6E illustrates a different view of FIG. 6C (some elements not shown for clarity). Specifically, object of interest 630 (illustrated in FIG. 6C as the femoral calcar) is shown positioned a vertical distance h above radiation receiver 604. Reference point 628 and anchor point 626 are separated by a distance $e_1$.

The distance $d_1$ may be known from a position feedback mechanism of the radiography system that includes the radiation source 600 and radiation receiver 604. Alternatively, the distance $d_1$ may be determined based on the calibration marker images 608 and 610, as described with respect to FIG. 6A. The distance $e_1$ shown in FIGS. 6C and 6E may be used in the same manner as the diameter and/or size of the image of the object of interest as described in any of the other embodiments described herein. The distance $e_1$ may be used to determine a height of the object of interest and, based on the height, determine the magnification of the image of the object of interest.

Specifically, by way of example, the magnification of the image 627 contained in radiograph 622 and/or a second image of the object of interest contained in a second radiograph (not shown) may be determined. The second image may be acquired from a second orientation where the second orientation is achieved by moving the radiation source 600 up or down from position 614 into a second position. In the second orientation, the radiation source 600 may be located a distance $d_2$ above the radiation receiver 604.

Calibration markers 602 and 606 may produce corresponding images and a line may be determined connecting the images. The line may have a length $2x_2$ and a midpoint of the line may be used as an anchor point in the second radiograph. The anchor point in radiograph 622 and the anchor point in the second radiograph may coincide with the same underlying anatomical feature depicted in the radiographs. Accordingly, the anchor point may be a stationary reference point that does not move relative to radiograph 622 and the second radiograph. A second distance $e_2$ (not shown) may be measured between the anchor point in the second radiograph and the reference point 627 (reference anatomical feature) of the second image of the object of interest contained in the second radiograph. Due to vertical movement of the radiation source in relation to the radiation receiver, the magnification of the second image of the object of interest and the position of the second image of the object of interest will be different in the second radiograph than in the first radiograph 622. Accordingly, the distances $e_1$ and $e_2$ will be different.

The height h of the object of interest 630 may be determined based on triangles 632 and 634 illustrated in FIG. 6E.

Specifically, based on triangles 632 and 634, the tangent of the angle $\theta_1$ may be expressed as Equations (43) and (44) respectively.

$$\tan(\theta_1) = \frac{b}{d_1 - h} \quad (43)$$

$$\tan(\theta_1) = \frac{e_1}{d_1} \quad (44)$$

Equations (43) and (44) may be combined into Equation (45) to solve for b, where b is the distance between the edge (reference point) of object of interest 630 and a line projecting from the radiation source 600 to anchor point 626. The magnification $M_1$ of the image 627 contained in radiograph 622 may be expressed according to Equation (14).

$$\frac{b}{d_1 - h} = \frac{e_1}{d_1} \quad (45)$$

$$b = \frac{e_1(d_1 - h)}{d_1}$$

An equivalent procedure may be carried out for the second image acquired with the radiation source at the second position. Based on the second image contained in the second radiograph, the distance b may also be expressed according to Equation (46) and the magnification $M_2$ of the image 612 may be expressed by Equation (15).

$$b = \frac{e_2(d_2 - h)}{d_2} \quad (46)$$

In order to determine the magnification of either image 627 or the second image contained in the second radiograph, example embodiments may determine the height h of the object 630 by combining Equations (45) and (46), resulting in Equation (47).

$$\frac{e_1(d_1 - h)}{d_1} = \frac{e_2(d_2 - h)}{d_2} \quad (47)$$

$$e_1 d_2 (d_1 - h) = e_2 d_1 (d_2 - h)$$

$$h = \frac{d_1 d_2 (e_2 - e_1)}{d_1 e_2 - d_2 e_1}$$

The height h may now be used with Equations (14) and (15) to determine the magnifications $M_1$ and $M_2$. The determined magnifications may be used to scale the corresponding images in order to determine the actual physical size of the object of interest 630. In general, any of the embodiments described herein may use a distance between an anchor point (stationary reference point) and a reference point in an image of an object of interest in place of a diameter, size, or other dimension of the object of interest when determining a height of the object of interest and/or a magnification of an image of the object of interest. The reference point and/or anchor point may be any identifiable point in the radiograph and is not limited to the examples provided herein. The elements of the embodiment described with respect to FIGS. 6C-6E may be combined with any of the other embodiments described, illustrated, or otherwise contemplated herein. Likewise, elements of all other embodiments described herein may be combined with the embodiment illustrated in FIGS. 6C-6E. The operations of the embodiment described with respect to FIGS. 6C-6E may be carried out by a computing device.

VI. Marker Positioning Overview

Figure 7:
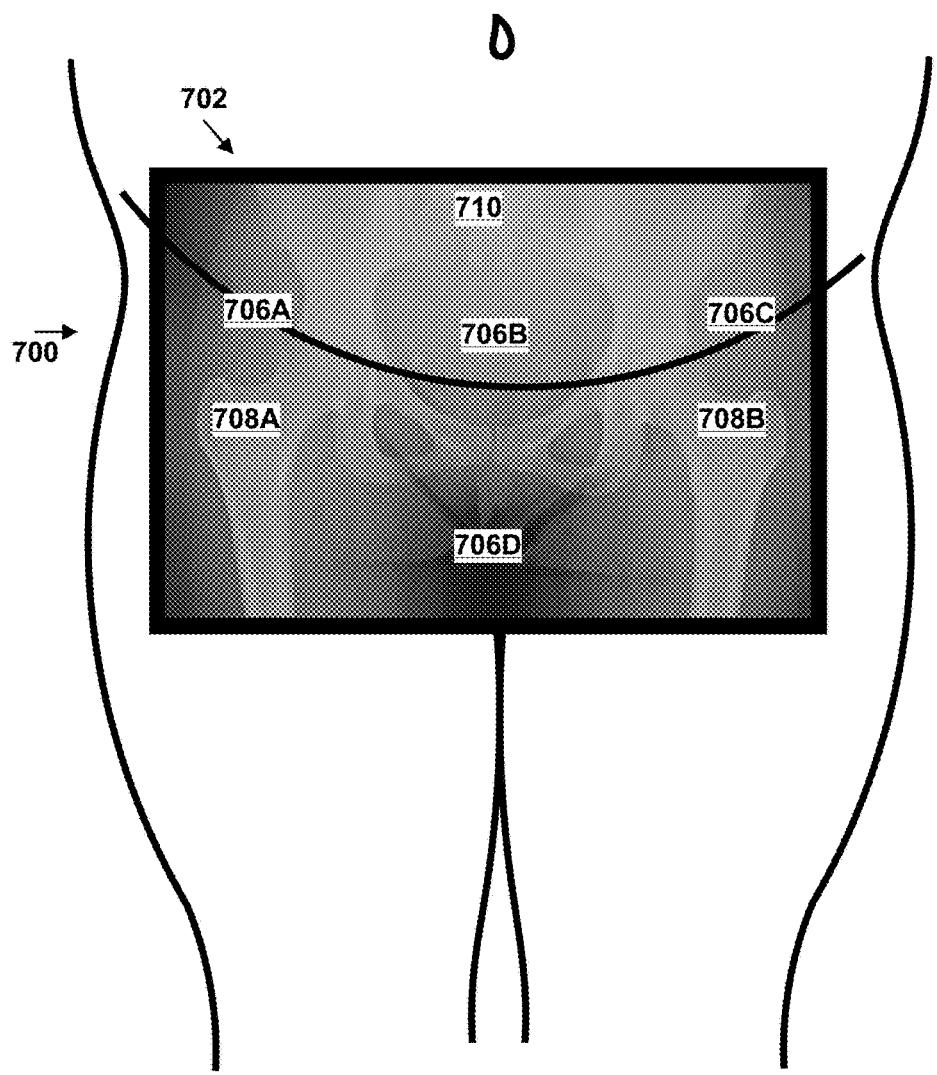
FIG. 7 illustrates an anteroposterior radiograph of a hip, according to an example embodiment.

FIG. 7 illustrates an example radiograph 702 of pelvic region 700 of a human. Radiograph 702 includes images of pelvis 710, right femur 708A, and left femur 708B. In order to scale the radiograph 702 and/or portions thereof according to magnifications corresponding to the different anatomical features shown in the radiograph 702, one or more calibration markers may be used at the time of capturing radiograph 702. The one or more calibration markers may be referred to as a calibration marker system. The one or more calibration markers may produce one or more corresponding images on radiograph 702 (not shown). The one or more calibration markers may have known measurements and/or spatial relationships relative to one another that may be used to determine the position and orientation of the radiation source with respect to the radiation receiver of a radiographic imaging device, as described herein.

However, in some instances, the images of the one or more markers may overlap with images of anatomical features, thus obscuring portions of the anatomical features. This may be especially problematic when a calibration marker system is used that includes a large number of calibration markers, includes large calibration markers (e.g., markers of comparable size to a size of anatomical features of interest), and/or the anatomical features of interest take up a large portion of the area of the radiograph. Overlap between images of calibration markers and anatomical features of interest may lead to errors in templating the obscured anatomical features, misdiagnoses, missed diagnoses, and/or improper treatment (e.g., missed cancerous tumor, avascular necrosis, fractured bone, etc.).

In some embodiments, the marker system may include a large number of calibration markers (e.g., three or more markers). It may be sufficient to capture images of at least two of the markers in order to determine the relative position and orientation between the radiation source and the radiation receiver, as discussed with respect to FIG. 5B. In some instances, however, improper positioning of the marker system may result in an insufficient number of the markers (e.g., only one marker) producing corresponding images on the radiograph (e.g., most markers might not be exposed to radiation from the radiation source due to improper positioning).

As a result, the patient might need to undergo repeated radiation exposure to acquire radiographs that include images of a sufficient number of calibration markers that do not obscure images of anatomical features of interest. Thus, precise, accurate, and reliable placement of the calibration markers is needed to capture satisfactory radiographs that can be used to diagnose and treat patients.

FIG. 7 further illustrates anatomical regions 706A, 706B, 706C, and 706D that, in the particular example of pelvic region 700, might serve as potential location where images of calibration markers may be located without obscuring anatomical features of interest. In particular, radiograph 702 may be captured to template the hips of the patient for a hip replacement prosthesis. Accordingly, all portions of pelvis 710, right femur 708A, and left femur 708B may need to be unobstructed by calibration markers in order to successfully template the hip. However, regions 706A (superior to right femur 708A), 706B (pelvic opening), 706C (superior to left femur 708B), and 706D (inferior to pelvis 710 and between femur 708A and femur 708B) might not be important in a medical diagnosis and may thus be candidate regions for calibration marker images.

The apparatuses and operations described herein aid in accurate and consistent positioning of calibration markers relative to a radiation source, a radiation receiver, and/or an object of interest (e.g., hips of a patient) to ensure that images of the calibration markers are produced in regions of radiographs that do not contain anatomical features of interest (e.g., regions 706A, 706B, 706C, and 706D in the example of a human hips) and/or regions that are not involved in a medical diagnosis.

The devices herein described do not require positioning or attaching the calibration marker system to a person (e.g., in the groin area 706D of a person). Thus the likelihood that proper radiographic imaging procedures are followed by the radiography technician and the patient may be increased (e.g., due to the technician not having to place markers in personal areas of the patient such as groin area 706D and due to not having to attach the markers to patients' bodies).

VII. Marker Positioning Apparatus Attachable to a Radiation Source

FIG. 8 illustrates one possible embodiment of a calibration marker positioning apparatus. The apparatus comprises one or more calibration markers 808 (e.g., calibration marker system), an extension arm 810, a mounting device 812, and a fastening mechanism 814. The marker positioning apparatus may be removably attachable, via mounting device 812, to a radiographic imaging device. Specifically, FIG. 8 illustrates the marker positioning apparatus attached to radiation source 800. The radiation source 800 and radiation receiver 804 may form, in whole or in part, the radiographic imaging device or system. The radiation source 800 may be configured to emit radiation onto the radiation receiver 804. The extent of the radiation beam produced by radiation source 800 is illustrated by lines 806a and 806b.

In some embodiments, the radiation source 800 may be located above radiation receiver 804 (vertically opposable orientation). In this configuration, a person may need to lie flat on the radiation receiver 804 when a radiograph of a portion of the person's body is captured. Alternatively, the radiation receiver 804 and radiation source 800 may be rotated by approximately 90 degrees (e.g., 80 to 100 degrees) from the position illustrated in FIG. 8 into a horizontally opposable orientation. In this horizontally opposable configuration, the person may stand between radiation source 800 and radiation receiver 804 when a radiograph of a portion of the person's body is captured. The example marker positioning devices disclosed herein may be adapted to and used with both vertically opposable and horizontally opposable radiographic imaging systems.

Calibration marker system 808 may include one or more radio-dense calibration markers of known sizes, separated from one another by known distances. Each of the markers may have the same or a different radio-density. Accordingly, each marker may produce, on the radiograph, a corresponding image having an image intensity corresponding to the radio-density of the marker. Consequently, the correspondence between markers and their images may be determined based on the correspondence between image intensity and the known marker radio-density. Alternatively, each of the calibration markers may be radiopaque, thus allowing minimal to no radiation to penetrate the calibration markers.

Further, within embodiments, a marker system may include one or more radio-dense calibration markers and/or one or more symbols or indicia. The symbols or indicia may indicate a perspective from which the radiograph was acquired, an exposure intensity, exposure type, and/or a type/model of the marker system used in capturing the radiograph.

The calibration marker system 808 may be connected to extension arm 810. The extension arm 810 may be connected to the radiographic imaging device (e.g., radiation source 800) via mounting device 812. The mounting device 812 may provide for translation of the extension arm with respect to radiographic imaging device in at least a first dimension. For example, the first dimension may be a sideways motion along line 816. Within examples, an extension arm may include one or more rods, linkages, shafts, leadscrews, pistons (e.g., hydraulic pistons, pneumatic pistons), bars, and/or strips of a rigid material as well as any equivalents or combinations thereof. The rigid material may be metal, plastic, rubber, wood, glass, equivalents thereof, composites thereof, and/or combinations thereof.

Additionally, within examples, a mounting device may comprise one or more clamps (e.g., C-clamps that clamp to a portion of the radiographic imaging device, lever release clamps, etc.), magnets (e.g., magnet that engage with a ferromagnetic portion of the radiographic imaging device), screws (e.g., screws through one or more holes on the mounting device that screw into one or more corresponding threaded holes on the radiographic imaging device), brackets, hooks (e.g., hooks that hook into one or more corresponding holes or loops on the radiographic imaging device), clasps, belts (e.g., belts that loop around a portion of the radiographic imaging apparatus), bands, adhesives, and/or fastening tapes (e.g., Velcro) removably attachable to the radiographic imaging apparatus (e.g., the radiation source 800 and/or the radiation receiver 804).

Further, within examples, a mounting device may attach, connect, or otherwise interface with one or more existing mechanical features of the radiographic imaging device. The one or more mechanical features of the radiographic imaging device may include slots, groves, rails, channels, threaded holes, and non-threaded holes, among other possibilities. The one or more mechanical features may be included on the radiographic imaging device for purposes other than attachment of the marker positioning system. The one or more mechanical features may be provided by the original equipment manufacturer or may be aftermarket parts used to modify the radiographic imaging device. For example, a radiation source may include two or more opposing slots or grooves configured to slidably receive therebetween a removable screen that includes one or more targeting lines used to position the radiation source with respect to a radiation receiver. In another example, the radiation receiver may include a rail on which a handle may be slidably connected. The handle may be used to aid in repositioning the radiation receiver. The mounting device may be configured to opportunistically use such existing mechanical features to removably attach the marker positioning device to the radiographic imaging device.

The mounting device may be firmly, but removably, affixed to the radiographic imaging device. Thus, any motion of the radiographic imaging device (e.g., radiation source 800 when the marker positioning apparatus is connected to radiation source 800) may also result in corresponding motion of the marker positioning apparatus. Accordingly, minimal to no adjustments of the marker positioning device may be needed between capturing subsequent radiographic images.

Fastening mechanism 814 may couple the extension arm 810 to mounting device 812. The fastening mechanism 814 may be operable between a locked operational configuration and an unlocked operational configuration. In the locked operational configuration, the fastening mechanism 814 may provide for retention of the extension arm 810 in a fixed position with respect to the mounting device 812. In the unlocked configuration, the fastening mechanism 814 may provide for translation of the extension arm 810 with respect to the mounting device 812 and the radiographic imaging device in at least the first dimension (e.g., along arrow 816). Within examples, a fastening mechanism may include one or more screws, thumbscrews (screws that can be tightened by hand, without a screw driver), ratchet and pawl mechanisms, ball and detent mechanisms, hasps, locking pins, rack and pinion mechanisms, and/or combinations or variations thereof. Other fastening mechanisms may be possible.

In some embodiments, translation of the extension arm 810 with respect to the mounting device 812 and the radiographic imaging device may be performed manually by a radiography technician or other medical professional. Specifically, the medical professional may place fastening mechanism 814 in the unlocked operational configuration and adjust the extension arm 810 to position the calibration marker system 808 in a desired position with respect to the radiographic imaging system. The medical professional may then place fastening mechanism 814 in the locked operational configuration to "lock-in" the desired position of the calibration marker system 808.

In alternative embodiments, the positioning of the calibration marker system 808 with respect to the radiographic imaging device may be aided by one or more motors and one or more corresponding gearboxes. In particular, a first motor (not shown) may be connected to the extension arm 810 through a first gearbox. The first motor may be configured to drive/reposition the extension arm 810 with respect to mounting device 812 in a first dimension and thus reposition the extension arm and the calibration markers 808 with respect to the radiographic imaging device. Similarly, the mounting device 812 may include a second motor (not shown) connected to the mounting device 812 through a second gearbox. The second motor may be configured to drive/reposition the mounting device 812 in a second dimension perpendicular and coplanar with the first dimension. Thus, the second motor may also reposition the extension arm and the calibration markers 808 with respect to the radiographic imaging device. The motors may be remotely controlled by a medical professional. Alternatively, the motors may be controlled by a computing device programmed to position the one or more calibration markers 808 in a particular position based on the size and/or type of radiographic image being captured and/or a size of the patient.

Figure 9A:
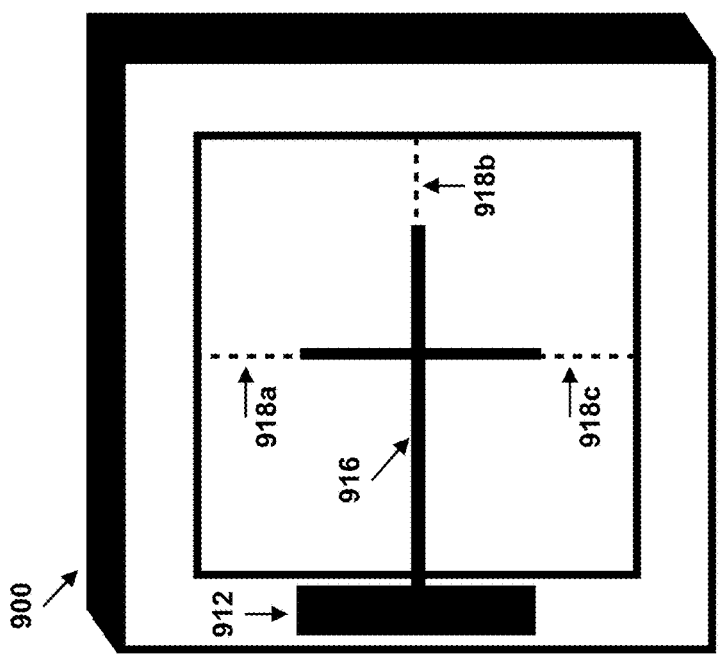
FIG. 9A illustrates example alignment features, according to an example embodiment.

The process of positioning maker system 808 with respect to the radiographic imaging system may be aided by one or more visual alignment features. The one or more visual alignment features may be configured to align the one or more radio-dense markers 808 relative to the radiographic imaging device. FIG. 9A illustrates one example of the one or more visual alignment features. Specifically, FIG. 9A illustrates an underside of radiation source 900. Radiation source 900 may include one or more targeting lines configured to project one or more corresponding visual reference lines onto a radiation receiver (e.g., radiation receiver 804 of FIG. 8). The one or more targeting lines may include line 918a, line 918b, and line 918c (as well as a fourth line hidden under extensions lines 916).

The one or more visual alignment features may include one or more extension lines 916 corresponding to the one or more targeting lines 918a, 918b, and 918c. The one or more extension lines 916 may be arranged in the same shape as the one or more targeting lines 918a-918c, as shown in FIG. 9A (e.g., a cross shape or T-shape). The extension lines 916 may be connected to the radiographic imaging device via mounting device 912. The extension lines 916 may form, in whole or in part, the extension arm (e.g., extension arm 810) to which one or more markers (not shown) are connected. Aligning the calibration marker system relative to the radiographic imaging device may include translating the extension arm and/or the mounting device 912 to line up the extension lines 916 with the targeting lines 918a-918c, as shown in FIG. 9A. In general, any of the alignment features described herein may include a ruler with numerical markings to aid in positioning and adjusting of the marker positioning apparatus. Further, when the marker positioning device is driven by one or more motors, the motors may include position feedback mechanisms that provide information about the relative position between the marker positioning device and the radiographic imaging apparatus.

Figure 9C:
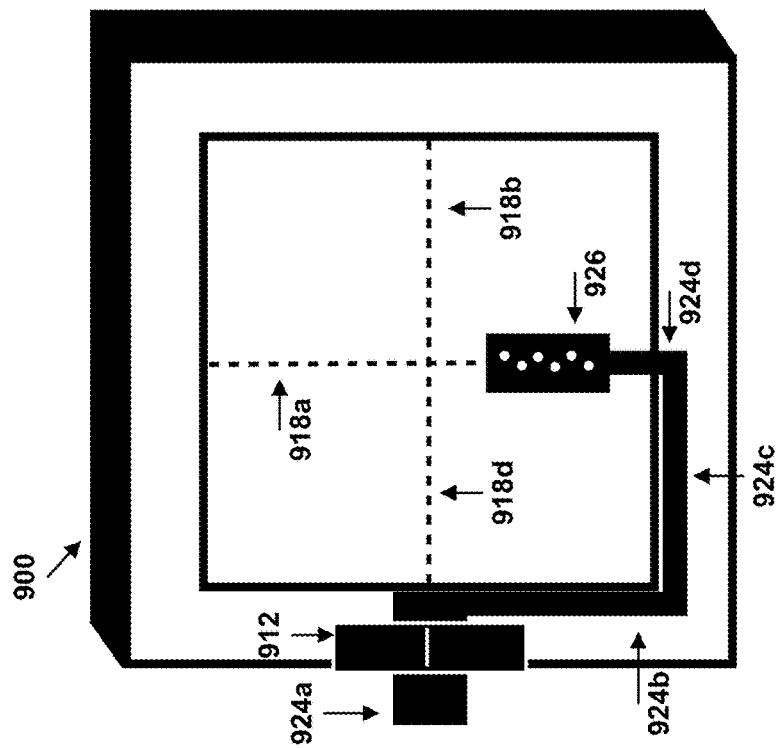
FIGS. 9B and 9C illustrates example marker positioning devices connected to radiation sources, according to an example embodiment.
Figure 9B:
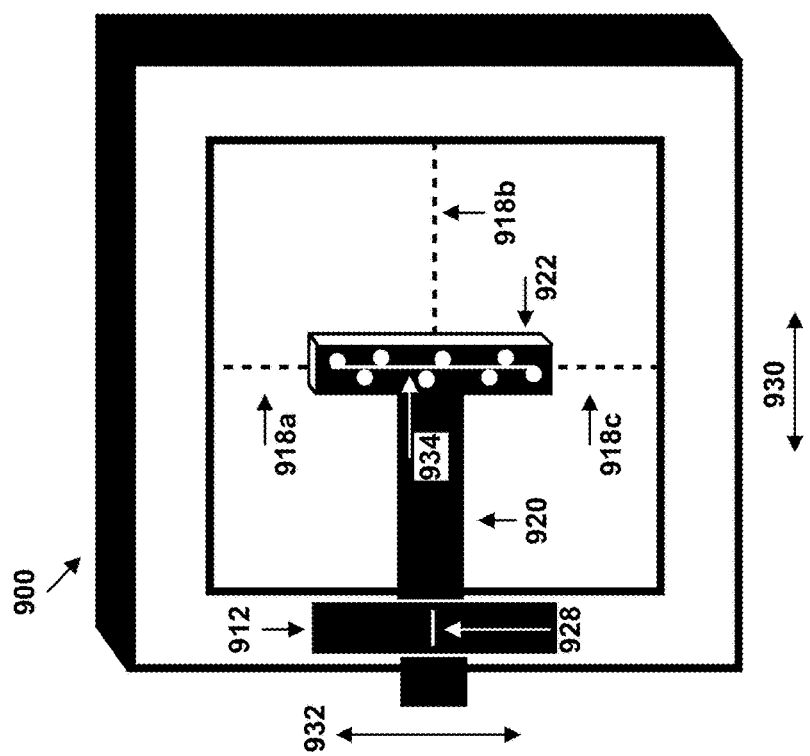

FIG. 9B illustrates a further embodiment of the marker positioning apparatus connected to radiation source 900 of a radiographic imaging device. In FIG. 9B, calibration marker system 922 is connected to extension arm 920. Extension arm 920 comprises a single linear rigid piece that is connected to the radiation source 900 via mounting device 912. Mounting device 912 may allow for translation of the extension arm in a first dimension 930. The mounting device may be slidably coupled to the radiation source 900 to provide for translation of the mounting device 912 with respect to the radiation source 900 in at least a second dimension 932. Mounting device 912 may interface with one or more exiting mechanical features of the radiation source 900 to removably attach the marker positioning apparatus to the radiation source 900.

The first dimension 930 may be perpendicular to and coplanar with the second dimension 932. The first dimension 930 and the second dimension 930 may both be perpendicular to a third dimension in which the radiation source 900 emits or is configured to emit radiation. Within examples, "perpendicular" is herein defined to encompass angles between 80 and 100 degrees. Thus, "perpendicular" may encompass variations in the relative orientation of two or more components caused by manufacturing imperfections, wear-and-tear, as well as clearances designed to allow the parts to operate smoothly relative to one another.

The mounting device 912 further includes visual alignment features 928 and 930. Visual alignment features 928 and 934 may be referred to as alignment lines, alignment markers, and/or positioning markers. Within examples, the visual alignment features may be primarily superficial features such as painted-on markings, stickers, and/or projections of light, among other possibilities. Further, within examples, the visual alignment features may be two-dimensional or three-dimensional topographical features such as etchings, tongues, grooves, and/or gaps, among other possibilities. Alignment line 928 may be lined up with targeting line 918b of the radiation source 900 to position the marker positioning apparatus in a desired position with respect to radiation source 900 along dimension 932.

The desired position may be a position that produces radiographic images without any overlap between images of calibration markers 922 and anatomical features of interest of a patient. Alignment line 934 may be lined up with targeting lines 918a and 918c to position the marker positioning apparatus in a desired position with respect to radiation source 900 along dimension 930. In some embodiments, the alignment feature 928 and/or 934 may be aligned with one or more physical features (e.g., etchings, gaps, or grooves) of the radiographic imaging apparatus. For example, one or more alignment tongues of the marker positioning apparatus may fit into one or more corresponding grooves on the radiographic imaging device. More generally, the alignment features of the marker positioning device may include one or more contoured mating surfaces configured to mate with one or more corresponding mating features on the radiographic imaging device.

In general, the alignment features may be located on any component of the marker positioning device provided that the alignment features allow for aligning one or more components of the marker positioning apparatus with one or more features of the radiographic imaging device. For example, alignment features may be included on any combination of the mounting device, the extension arm, fastening mechanisms, and/or the calibration marker system.

FIG. 9C illustrates an alternative implementation of the marker positioning apparatus. Specifically, FIG. 9C illustrates an alternative implementation of the extension arm that reduces or eliminates overlap between the extension arm and the surface of radiation source 900. In contrast to FIG. 9C, extension arm 920 of FIG. 9B is comprised of a single linear section that overlaps with a portion of the surface of the radiation source 900. Radiation emitted from radiation source 900 may be absorbed by the portion of extension arm 920 that overlaps with the surface of the radiation source 900. Accordingly, the overlapping portion of extension arm 920 may appear on the captured radiographic image, potentially obscuring anatomical features of interest. In some embodiments, the extension arm 920 may be made of a radiolucent material that does not absorb radiation produced by radiation source 900 (e.g., radiation may penetrate the radiolucent material much more easily than it penetrates anatomical features of interest, thus producing no discernable image on the radiograph).

However, even when radiolucent materials are used to construct the extension arm, the structure of the extension arm may still be designed to reduce and/or minimize obstruction of the radiation source 900 by the extension arm. For example, overlap between the extension arm and the radiation source may be reduced or minimized to ensure that the projections of the targeting lines 918a, 918b, and 918c of the radiation source are not obstructed by the extension arm. Specifically, as shown in FIG. 9C, the extension arm may be constructed of four linear sections 924a, 924b, 924c, and 924d that follow the contours of the radiation source 900. The first extension arm section 924a may be configured to translate with respect to mounting device 912 along dimension 930. Translation of the calibration marker system 926 along dimension 932 may be achieved via translation of the mounting device 912 with respect to radiation source 900 using any of the mechanisms previously discussed.

In some embodiments, sections 924a-924d may be non-linear (e.g., curved) to allow for the contours of the radiographic imaging device to be more closely approximated by the extension arm. Further, any of the embodiments of the marker positioning devices herein described may utilize an extension arm that includes multiple linear, curved, and/or angled sections that reduce or minimize an extent of overlap between the extension arm and the radiation source and/or the radiation receiver.

Figure 10:
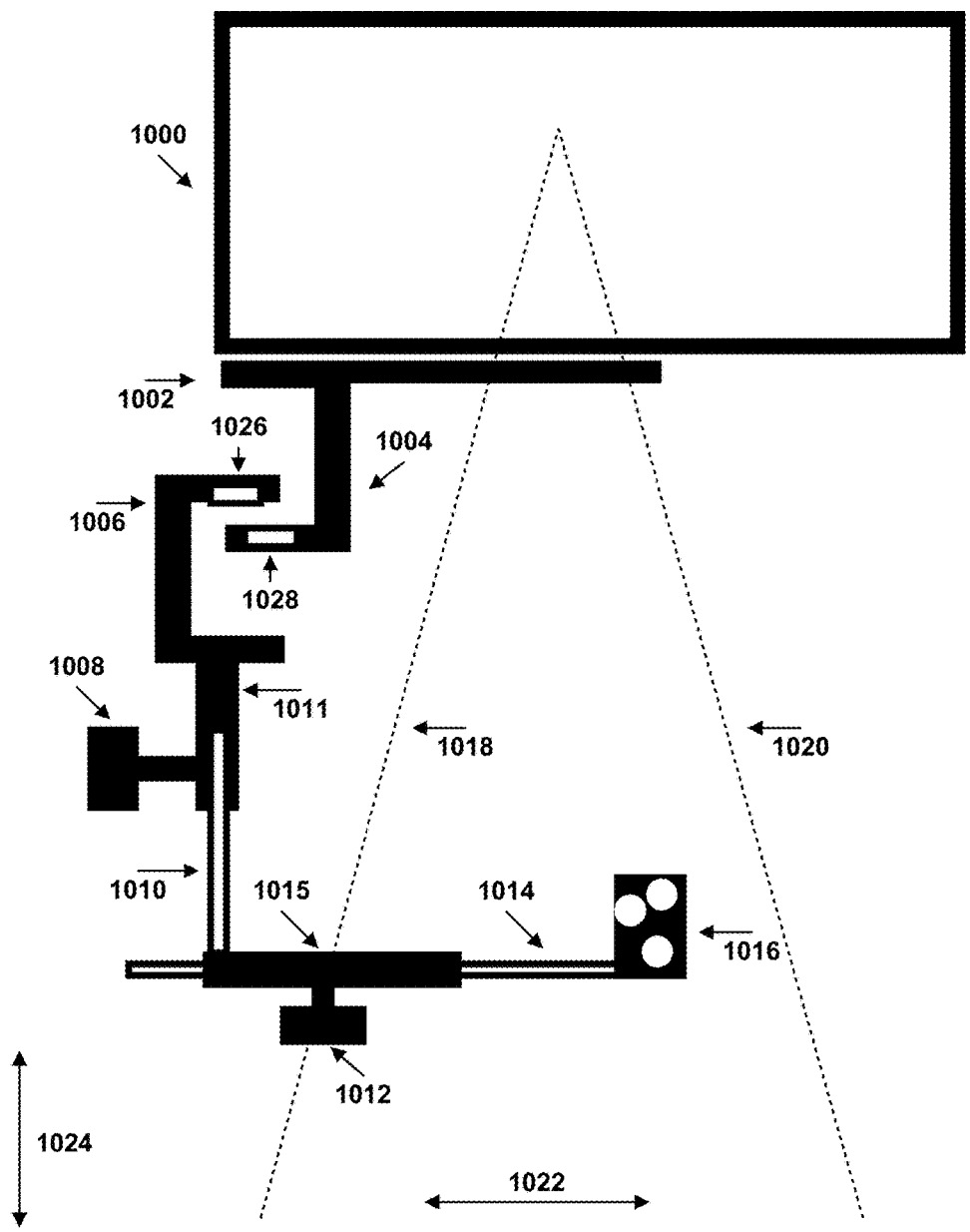
FIG. 10 illustrates an example marker positioning device movable with three degrees of freedom, according to an example embodiment.

FIG. 10 illustrates another example embodiment that includes a post interposed between the extension arm and the mounting device to allow adjustments of the position of the calibration markers in a third dimension perpendicular to the first dimension and the second dimension. Specifically, FIG. 10 illustrates an example marker positioning apparatus connected to radiation source 1000. The marker positioning apparatus is configured to adjust and maintain the position of calibration markers 1016 in three dimensions with respect to radiation source 1000. The capability of positioning the marker system 1016 in three dimensions allows the calibration marker system to be used in accordance with physician preferences as well as patient body habitus needs. For example, in obese patients, the marker system 1016 may need to be placed further away from the radiation receiver to clear the body of the obese patient.

Calibration markers 1016 may be connected to extension arm 1014. Extension arm 1014 may be connected to post 1010 and may be configured to translate with respect to post 1010 along dimension 1022. Extension arm 1014 may be connected to post 1010 through a coupling 1015. The extension arm 1014 and coupling 1015 may form a mechanism that allows the extension arm to translate along dimension 1022. For example, extension arm 1014 may include a rod that fits slidably into shaft 1015, or vice versa. Alternatively, extension arm 1014 and coupling 1015 may form a telescopic piston that provides for translation of extension arm 1014 along dimension 1022. Within examples, the term "extension arm" may encompass both portions 1014 and 1015.

A fastening mechanism 1012 may be operable between a locked and an unlocked position to allow for adjustments in the position of extension arm 1014 along dimension 1022 and for extension arm 1014 to be locked firmly into a fixed position. As previously discussed, the fastening mechanism may include screws, thumb screws, ratchet and pawl mechanisms, ball and detent mechanisms, hasps, locking pins, rack and pinion mechanisms, and/or combinations thereof. Other mechanisms may be possible.

Post 1010 may be connected to mounting device 1002. In particular, post 1010 may be connected to mounting device 1002 through coupling 1011. Similar to the extension arm 1014, the post 1010 and coupling 1011 may form a mechanism that allows the post 1010 to translate along dimension 1024. For example, post 1010 may include a rod that fits slidably into shaft 1011 and is locked in place via one or more screws or pins, or vice versa. Alternatively, post 1010 and coupling 1011 may form a telescopic piston that provides for translation of post 1010 along dimension 1024. Within examples, the term "post" may encompass both portions 1010 and 1011. Further, within examples, a post may include one or more rods, linkages, shafts, leadscrews, pistons (e.g., hydraulic pistons, pneumatic pistons), bars, and/or strips of a rigid material as well as any equivalents or combinations thereof. The rigid material may be metal, plastic, rubber, wood, glass, equivalents thereof, composites thereof, and/or combinations thereof.

A fastening mechanism 1008 may be operable between a locked and an unlocked position to allow for adjustments in the position of post 1010 along dimension 1024 and for post 1010 to be locked firmly into a fixed position.

Mounting device 1002 may include a first mounting section 1004 and a second corresponding mounting section 1006. The first and second mounting sections 1004 and 1006 may be "L-shaped" or hook-shaped to allow for coordinated engagement and retention of the first and second mounting sections 1004 and 1006 with respect to one another. First mounting section 1004 may include a first coupling 1028. Second mounting section 1006 may include a second coupling 1026. Coupling 1026 may engage with coupling 1028 to couple mounting sections 1004 and 1006 together.

Couplings 1026 and 1028 may include contoured mating surfaces. Specifically, coupling 1026 may include a positive contoured feature (e.g., a protruding geometric feature) that fits into a negative mating feature (e.g., a recessed geometric feature) of coupling 1028. Couplings 1028 and 1026 may further include magnets that generate a force to interlock and mate couplings 1028 and 1026 together, thus mating hook portions 1026 and 1028 together. Alternatively or additionally, the couplings 1026 and 1028 may include adhesives or fastening tapes such as Velcro that aid in connecting couplings 1026 and 1028 together.

Thus, mounting device 1002 may, in some embodiments, include two distinct, connectable sections/portions (e.g., first portion 1004 and upper portion 1006). When a patient is attempting to lie down on or stand adjacent to a radiation receiver, the second portion 1006 may be disconnected from the first portion 1004. Since the second portion 1006 has connected thereto post 1010, extension arm 1014, and calibration markers 1016, removing the second portion 1006 prevents these portions of the marker positioning device from interfering with the patient as the patient is positioned relative to the radiation receiver. When the patient is positioned into a desired position and orientation, the second portion 1006 may be reattached to the first portion 1004. The apparatus may then be used to position markers 1016 into a desired position with respect to the radiation source 1000, the radiation receiver, and/or the patient's anatomy.

Further, the mounting device 1002 may be removably attachable to radiation source 1000 via any of the mechanisms previously discussed. Specifically, the portion of the mounting device indicated by arrow 1002 may be removably attachable to the radiation source 1000. Thus, there may be two or more distinct ways of disconnecting the mounting device from radiation source 1000. A partial disconnection may involve disconnecting first mounting portion 1004 from second mounting portion 1006 while keeping the first mounting portion 1004 attached to the radiation source 1000. A complete disconnection may involve disconnecting the entire mounting device 1002 (e.g., including first portion 1004) from the radiation source 1000.

The connection between mounting device 1002 and radiation source 1000 may provide for translation of the mounting device 1002 with respect to the radiation source 1000 in a dimension perpendicular to dimensions 1024 and 1022 (e.g., a direction coming out of the page of FIG. 10). Collectively, translation of the extension arm 1014, post 1010, and mounting device 1002 may provide for control over the spatial position of calibration markers 1016 in three dimensions.

In some embodiments, mounting device 1002 may interface with one or more exiting mechanical features of the radiation source 1000 to removably attach the marker positioning apparatus to the radiation source 1000. In other embodiments, a portion of the mounting device 1002 may be rigidly and/or permanently connected to the radiographic imaging device. A second portion of the mounting device may be removably attachable to the first portion to allow for removable attachment of the marker positioning device to the radiographic imaging apparatus. The connection between the first portion and the second portion may provide for translation of the marker positioning device with respect to the radiation source 1000 in a dimension perpendicular to dimensions 1024 and 1022. For example, first mounting portion 1004 may be rigidly and/or permanently attached to radiation source 1000. Second mounting portion 1006 may be removably attachable to first mounting portion 1004 via couplings 1028 and 1026. Couplings 1028 and 1026 may provide for translation of the marker positioning device with respect to the radiation source 1000 in a dimension perpendicular to dimensions 1024 and 1022. Other combinations and variations may be possible.

The components of the marker positioning device illustrated in FIG. 10, as well as the marker positioning devices described and illustrated in any of the other embodiments herein, may be constructed of a rigid material such as metal, plastic, rubber, wood, glass, carbon-fiber, composites thereof, and/or combinations thereof. The rigid construction may ensure that, once the positioning device is adjusted into a desired position, the positioning device maintains this desired position. Specifically, rigidity of the marker positioning device may ensure that vibrations, shocks, perturbations, and other disturbances (e.g., a patient accidentally hitting the marker positioning device) do not alter the position of the calibration markers relative to the radiation source and/or the radiation receiver. Further, portions of the marker positioning apparatus may be constructed from a radiolucent material that is easily penetrable by imaging radiation (e.g., X-Rays) and does not produce a corresponding image on the radiograph (e.g., a carbon-fiber reinforced plastic).

VIII. Marker Positioning Apparatus Attachable to a Radiation Receiver

Figure 11:
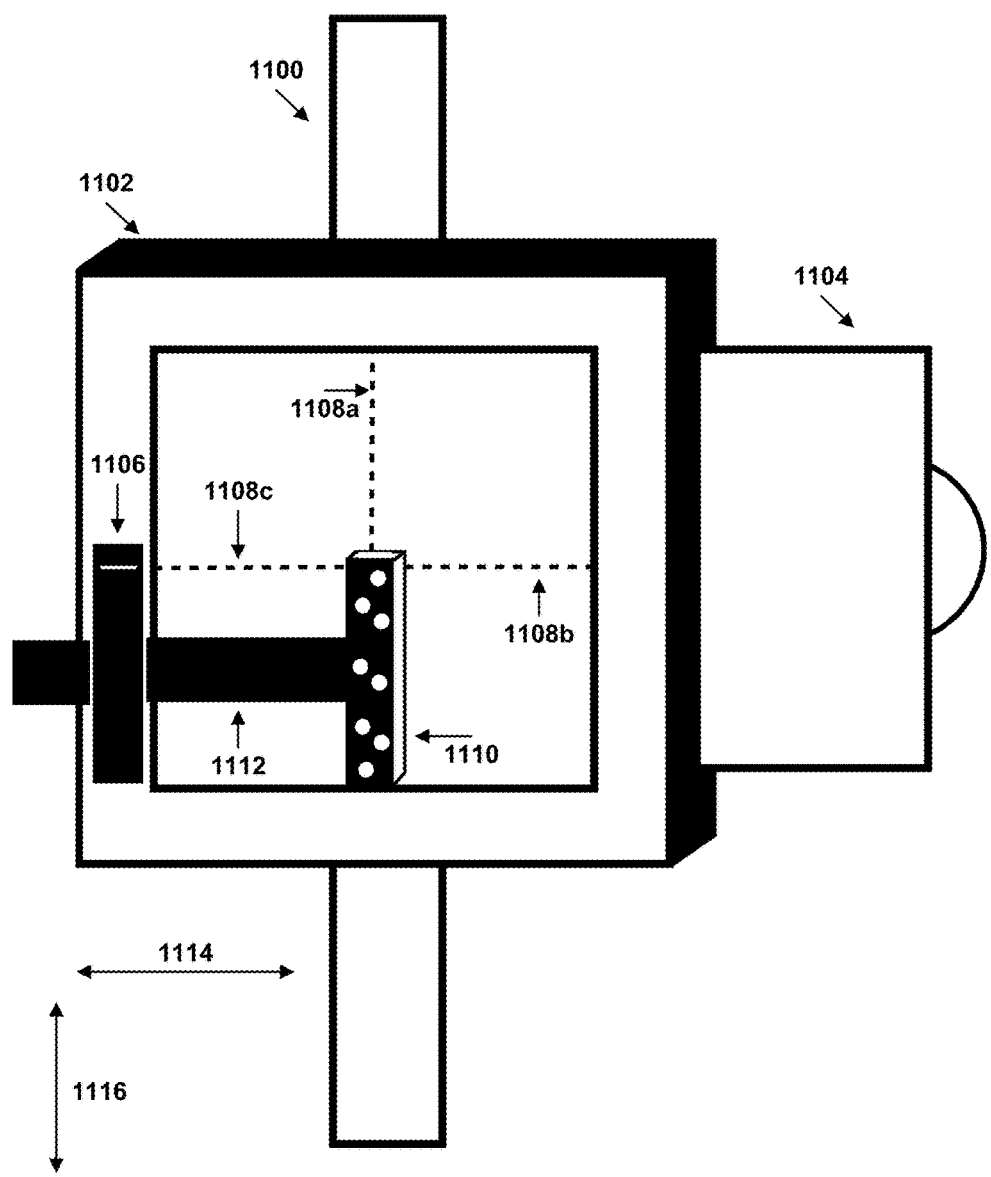
FIG. 11 illustrates an example marker positioning device connected to a radiation receiver, according to an example embodiment.

FIG. 11 illustrates an example marker positioning device that may be removably attachable to a radiation receiver. Specifically, FIG. 11 illustrates radiation receiver 1102 connected to a structural support 1100. Structural support 1100 may retain radiation receiver in an upright vertical position. Support 1100 and radiation receiver 1102 may be collectively referred to as a "bucky" or "wall bucky." Radiation receiver 1102 may include a radiographic film/cassette holder 1104. Radiation receiver 1102 may include targeting lines 1108*a*, 1108*b*, and 1108*c* (as well as a fourth line hidden under marker system 1110) that may be used to position a patient with respect to the radiation receiver 1102. The marker positioning apparatus may be connected to radiation receiver 1102 through mounting device 1106. Calibration markers 1110 may be connected to extension arm 1112. Extension arm 1112 may be connected to mounting device 1106. Mounting device 1106 may provide for translation of extension arm 1112 in a first dimension 1114 with respect to radiation receiver 1102.

Targeting lines 1108*a*-1108*c* may be used as reference points for the one or more calibration markers 1110. Specifically, mounting device 1106 may include alignment features corresponding to targeting lines 1108*b* and 1108*c* that may be used to align mounting device 1106 with respect to radiation receiver 1102 along dimension 1116. Similarly, extension arm 1112 may include one or more alignment features corresponding to line 1108*a* that may be used to align the extension arm 1112 with respect to radiation receiver 1102 along dimension 1114 (e.g., a center line of marker system 1110 itself may be aligned with line 1108*a*). The embodiment of FIG. 11 may be modified in a manner similar to that described with respect to FIG. 9C to reduce, minimize, or eliminate overlap between extension arm 1112 and radiation receiver 1102.

Figure 12B:
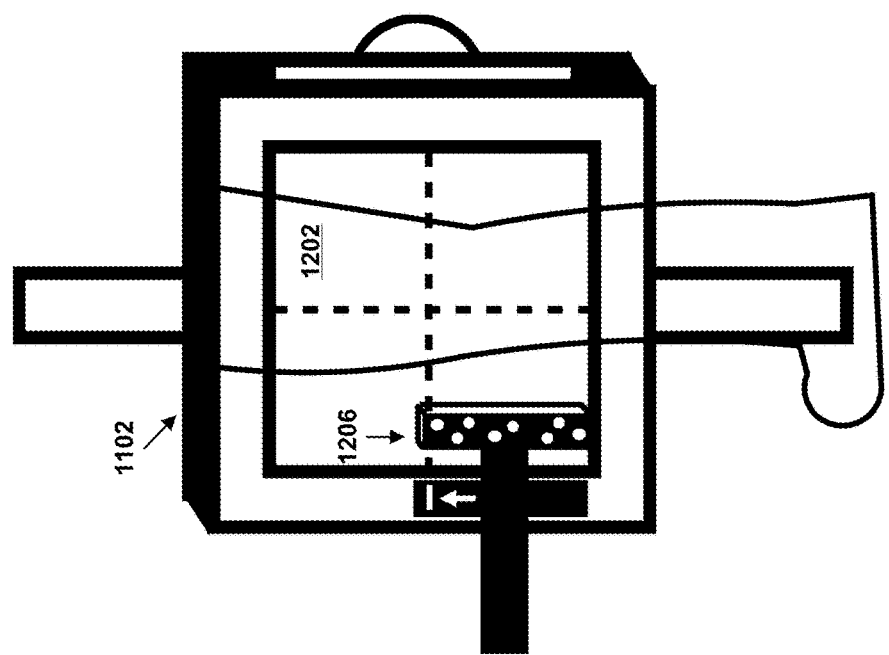
FIGS. 12A and 12B illustrate example positioning of a calibration marker system, according to an example embodiment.
Figure 12A:
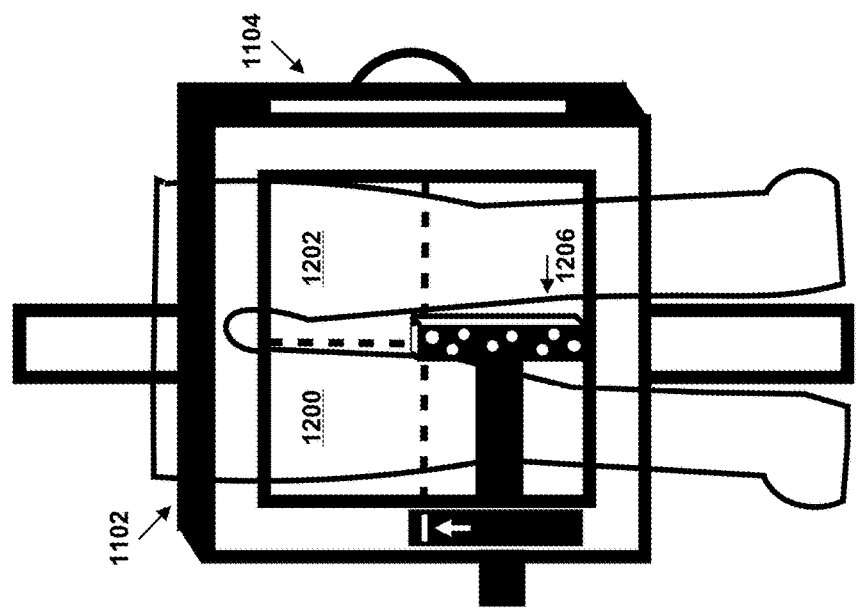

FIGS. 12A and 12B illustrate how the marker positioning device of FIG. 11 may be positioned to reduce or eliminate overlap between the calibration markers and anatomical features while ensuring that the calibration markers appear in the captured radiograph. Specifically, FIG. 12A illustrates radiation receiver 1102 being used to capture an anteroposterior radiograph of human knees. Specifically, an outline of a person's right and left legs 1200 and 1202, respectively, is shown overlapping the radiation receiver 1102 to illustrate a position that the person might be guided into to capture the anteroposterior knee radiograph. Calibration marker positioning device 1206 may be adjusted into a position, as shown, such that the calibration markers are located between the right and left legs 1200 and 1202, respectively, of the person undergoing the imaging process. Thus, potential for overlap between the calibration markers and any anatomical features of interest may be minimized or eliminated.

FIG. 12B illustrates radiation receiver 1102 being used to capture a lateral radiograph of human knees. Specifically, an outline of a person's left leg 1202 is shown overlapping the radiation receiver 1102 to illustrate a position that the person might be guided into to capture the lateral knee radiograph. Calibration marker positioning device 1206 may be adjusted into a position, as shown, such that the calibration markers are located in front of the legs of the person undergoing the imaging process. Thus, potential for overlap between the calibration markers and any anatomical features of interest may likewise be minimized or eliminated.

The marker positioning device may be used in the process of imaging any other body parts of a patient in any position that may be convenient for the patient and/or requested by the physician. The methods and devices herein described are not limited to human patients. The positions of the marker positioning device 1206 may be modified according to the body part being imaged. Standardized procedures may be developed to ensure medical professionals place the calibration markers in positions that are less likely to obscure anatomical features of interest and more likely to ensure that images of the calibration markers are produced on the radiograph.

Figure 13:
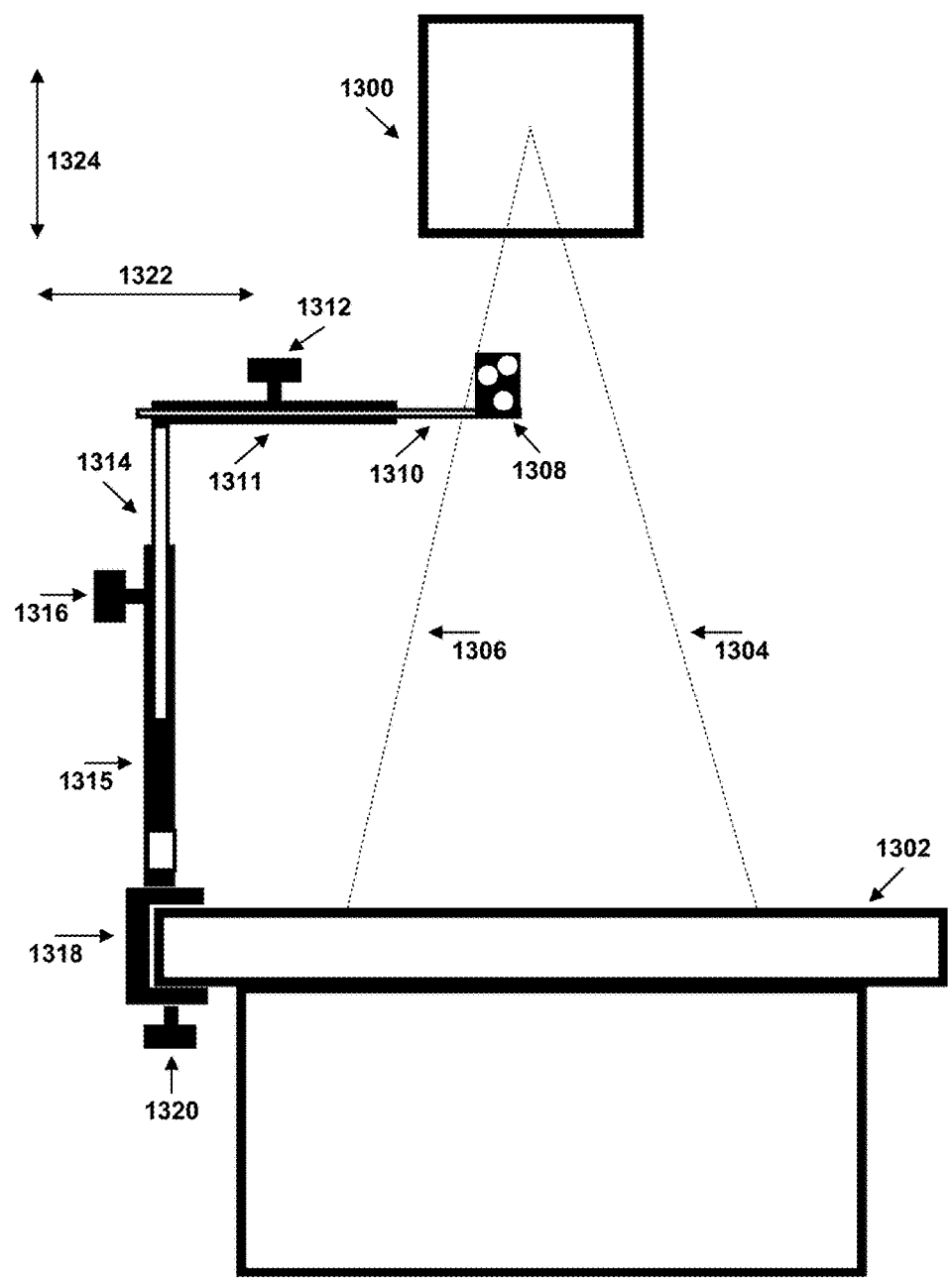
FIG. 13 illustrates another example marker positioning system movable in three degrees of freedom, according to an example embodiment.

FIG. 13 illustrates another example embodiment of a marker positioning stand connected to a radiation receiver. The marker positioning stand includes a post interposed between the extension arm and the mounting device to allow for adjustments of the position of the calibration markers in a third dimension perpendicular to the first dimension and the second dimension. Specifically, FIG. 13 illustrates an example marker positioning apparatus connected to radiation receiver 1302. Radiation receiver 1302 may be part of a radiographic imaging device that also includes radiation source 1300. The marker positioning apparatus may be configured to adjust and maintain the position of calibration markers 1308 in three dimensions with respect to radiation receiver 1302. Calibration markers 1308 may be connected to extension arm 1310. Extension arm 1310 may be connected to post 1314 and may be configured to translate with respect to post 1314 along dimension 1322. Extension arm 1310 may be connected to post 1314 through a coupling 1311. The extension arm 1310 and coupling 1311 may form a mechanism that allows the extension arm to translate along dimension 1322. For example, extension arm 1310 may include a rod that fits slidably into shaft 1311, or vice versa, and is locked in place using one or more screws or pins. Alternatively, extension arm 1310 and coupling 1311 may form a telescopic piston that provides for translation of extension arm 1310 along dimension 1322. Within examples, the term "extension arm" may encompass both portions 1310 and 1311.

A fastening mechanism 1312 may be operable between a locked and an unlocked position to allow for adjustments in the position of extension arm 1310 along dimension 1322 and for extension arm 1310 to be locked firmly into a fixed position. Fastening mechanism 1312 may include any of the previously discussed fastening mechanisms.

Post 1314 may be connected to mounting device 1318. In particular, post 1314 may be connected to mounting device 1318 through coupling 1315. Similar to the extension arm 1310, the post 1314 and coupling 1315 may form a mechanism that allows the post 1314 to translate along dimension 1324. For example, post 1314 may include a rod that fits slidably into shaft 1315, or vice versa. Alternatively, post 1314 and coupling 1315 may form a telescopic piston that provides for translation of post 1314 along dimension 1324. Within examples, the term "post" may encompass both portions 1314 and 1315. A fastening mechanism 1316 may be operable between a locked and an unlocked position to allow for adjustments in the position of post 1314 along dimension 1324 and for post 1314 to be locked firmly into a fixed position.

Mounting device 1318 may be removably connected to radiation source 1302 via any of the mechanisms previously discussed. The connection between mounting device 1318 and radiation receiver 1302 may provide for translation of the mounting device 1318 with respect to the radiation receiver 1302 in a dimension perpendicular to dimensions 1324 and 1322 (e.g., a direction coming out of the page of FIG. 13). Collectively, translation of the extension arm 1310, post 1314, and mounting device 1318 may provide for control over the spatial position of calibration markers 1308 in three dimensions.

Another fastening mechanism 1320 may be operable between a locked and an unlocked position to allow for adjustments in the position of mounting device 1318 along the third dimension and for mounting device 1318 to be locked firmly into a fixed position. Fastening mechanism 1320 may include any of the previously discussed fastening mechanisms.

IX. Example Orthographic Projections of Marker Positioning Devices

Figure 14C:
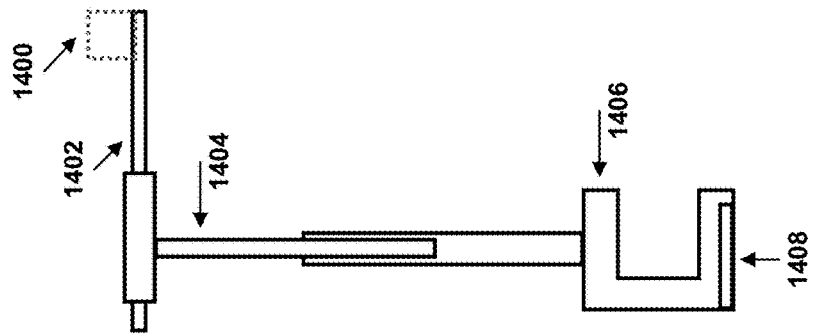
FIGS. 14A, 14B, and 14C illustrate orthographic projections of an example marker positioning device, according to an example embodiment.
Figure 14B:
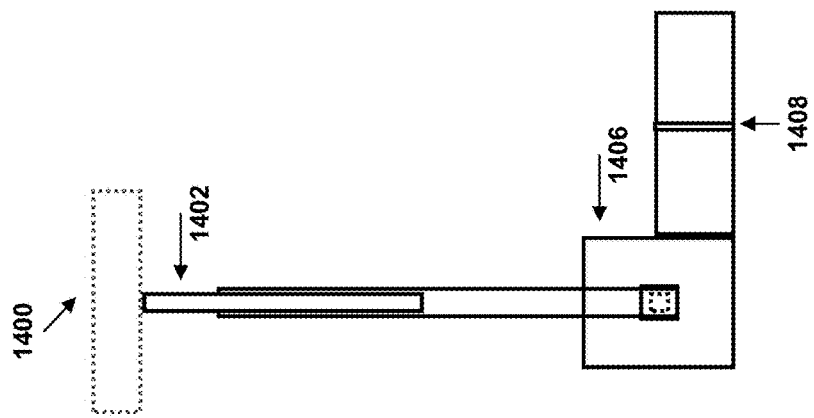
Figure 14A:
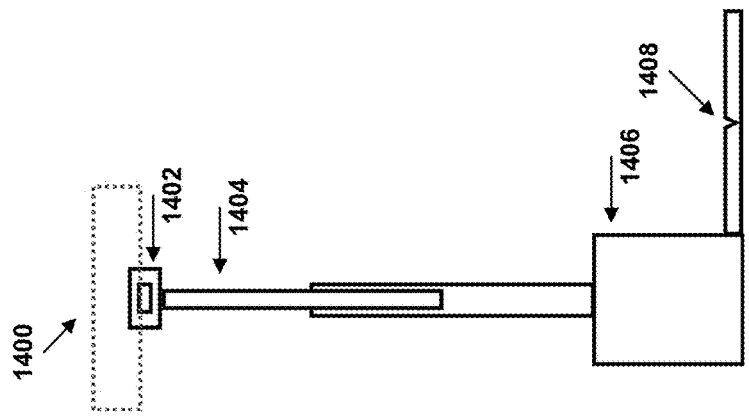

FIGS. 14A, 14B, and 14C illustrate orthographic projection drawings of another example marker positioning stand. In particular, FIG. 14A illustrates a front projection, FIG. 14B illustrates a top projection, and FIG. 14C illustrates a side projection. The marker positioning stand includes a marker system 1400. The marker system 1400 may be connected to first end of an extensions arm 1402. The extension arm 1402 may be connected, at a second end thereof, to a first end of post 1404. A second end of post 1404 may be connected to a mounting device 1406. Mounting device may be removably attachable to a radiographic imaging device. For example, mounting device 1406 may be removably attachable to a radiation source or a radiation receiver.

Mounting device 1406 may have connected thereto an alignment feature 1408. Alignment feature 1408 may include a flat portion having a groove therein. The groove may be aligned with one or more targeting lines of a radiation receiver or a radiation source to align the marker positioning device with respect to the radiation receiver or the radiation source. Alternatively, the groove may be aligned with a projection of the one or more targeting lines (e.g., a projection from the radiation source onto the radiation receiver) and/or one or more corresponding tongues on the radiographic imaging device (e.g., tongues that fit into the groove of alignment feature 1408).

Collectively, the extension arm 1402, the post 1404, and the mounting device 1406 may provide for positioning of the calibration marker system 1400 with respect to a radiographic imaging device in three dimensions. Specifically, extension arm 1402 may be configured to translate in a first dimension. Post 1404 may be configured to translate in a second dimension perpendicular to the first dimension. Mounting device 1406 may be configured to translate in a third dimension perpendicular to the first dimension and the second dimension.

Figure 15C:
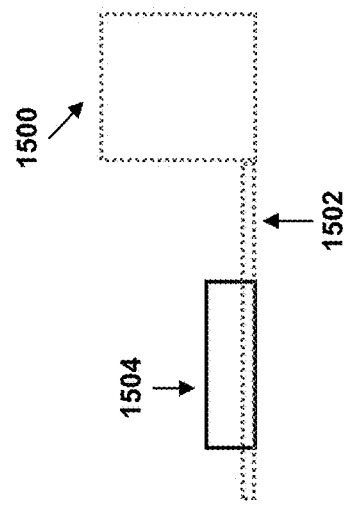
FIGS. 15A, 15B, and 15C illustrate orthographic projections of another example marker positioning device, according to an example embodiment.
Figure 15B:
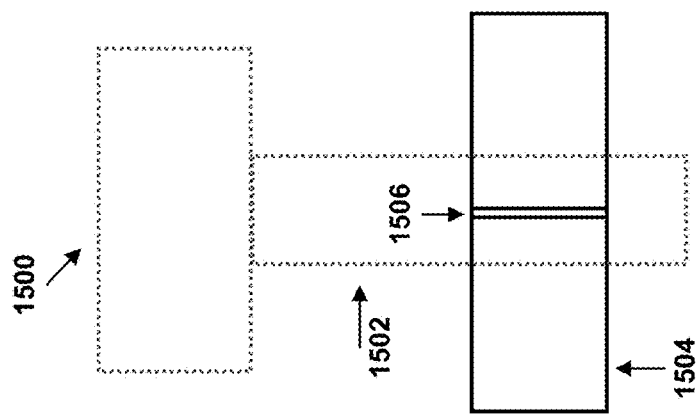
Figure 15A:
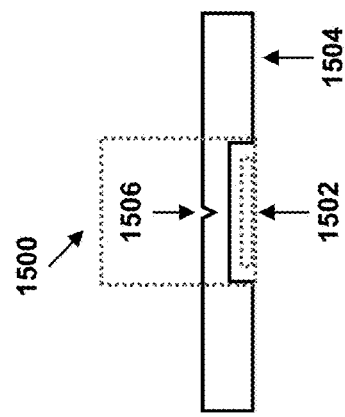

FIGS. 15A, 15B, and 15C illustrate orthographic projection drawings of a further example marker positioning stand. In particular, FIG. 15A illustrates a front projection, FIG. 15B illustrates a top projection, and FIG. 15C illustrates a side projection. The marker positioning stand includes a marker system 1500. The marker system 1500 may be connected to first end of an extensions arm 1502. The extension arm 1502 may be connected, at a second end thereof, to a mounting device 1504. Mounting device 1504 may be removably attachable to a radiographic imaging device. For example, mounting device 1504 may be removably attachable to a radiation source or a radiation receiver.

Mounting device 1504 may include an alignment feature 1506. Alignment feature 1506 may comprise a groove in the mounting device 1504. The groove may be aligned with one or more targeting lines of a radiation receiver or a radiation source to align the marker positioning device with respect to the radiation receiver or the radiation source. Alternatively, the groove may be aligned with a projection of the one or more targeting lines (e.g., a projection from the radiation source onto the radiation receiver) and/or one or more corresponding tongues on the radiographic imaging device (e.g., tongues that fit into the groove 1506).

X. Example Operations of a Marker Positioning Apparatus

Figure 16:
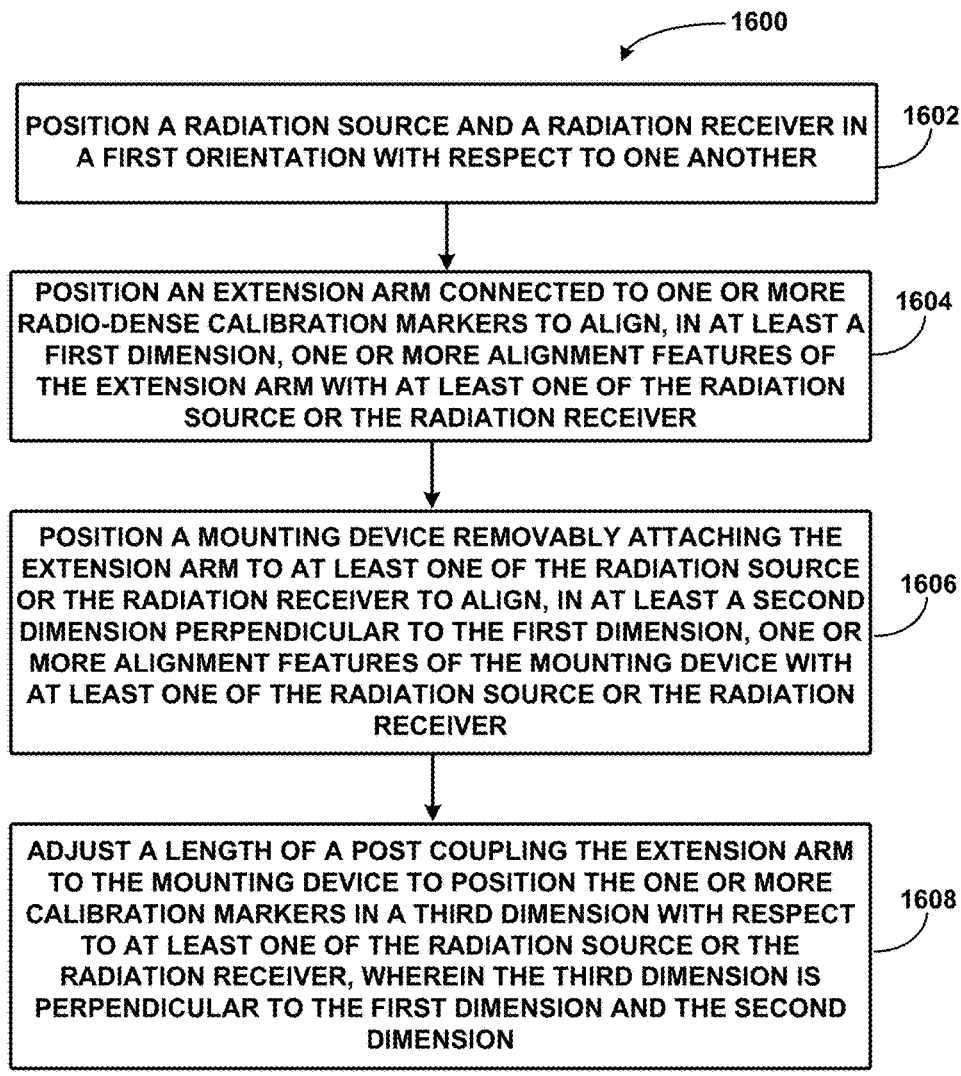
FIG. 16 illustrates a flow diagram of example operations, according to an example embodiment.

FIG. 16 illustrates a flow diagram 1600 of example operations that may be performed to position any of the marker positioning devices described herein relative to a radiographic imaging device. The operations may be performed by a medical professional. The medical professional may manually adjust the marker positioning device to place the markers in a desired position relative to the radiographic imaging apparatus. The desired position may be a position such that images of the calibration markers do not overlap with anatomical features of interest of a patient when a radiograph of taken. Alternatively, in embodiments equipped with motors, medical professional may use a remote control device to command one or more motors to position the marker positioning apparatus in the desired position with respect to the radiographic imaging device. In some embodiments, a computing device may be programmed to automatically cause the one or more motors of the marker positioning apparatus to move the positioning apparatus into the desired position. The desired position may be based on a type of radiographic image being captured (e.g., anteroposterior hip radiograph, lateral hip radiograph, anteroposterior knee radiograph, lateral knee radiograph, etc.).

In block 1602, a radiation source and a radiation receiver may be positioned in a first orientation with respect to one another. The first orientation may be selected based on a type, size, and/or perspective of the desired radiograph. In one example, the first orientation may include positioning the radiation source above the radiation receiver (e.g., in a vertically opposing configuration). In another example, the first orientation may include positioning the radiation source at the same height as the radiation receiver with a patient standing therebetween (e.g., in a horizontally opposing orientation).

In block 1604, an extension arm connected to one or more radio-dense calibration markers may be positioned to align, in at least a first dimension, one or more alignment features of the extension arm with at least one of the radiation source or the radiation receiver. The one or more alignment features of the extension arm may include markings, stickers, light projections, tongues, grooves, or etchings included on the extension arm as well as any other variations or combinations of the alignment features herein described. The one or more alignment features of the extension arm may be included directly on the extension arm and/or may include one or more features connected to the extension arm.

In general, the one or more alignment features of the marker positioning stand may be lined up with one or more features of the radiographic imaging device. For example, the alignment features of the marker positioning device may be lined up with one or more targeting lines of a radiation source and/or a radiation receiver. In another example, the alignment features of the marker positioning stand may be lined up with projections of the one or more targeting lines of the radiation source and/or the radiation receiver (e.g., shadows created by shining light over the targeting lines).

In block 1606, a mounting device removably attaching the extension arm to at least one of the radiation source or the radiation receiver may be positioned to align, in at least a second dimension perpendicular to the first dimension, one or more alignment features of the mounting device with at least one of the radiation source or the radiation receiver. The one or more alignment features of the mounting device may be visual alignment features such as markings, stickers, grooves, or etchings included on the mounting device as well as any other variations or combinations of the alignment features herein described. The one or more alignment features of the mounting device may be included directly on the mounting device and/or may include one or more features connected to the extension arm.

In block 1608, a length of a post coupling the extension arm to the mounting device may be adjusted to position the one or more calibration markers in a third dimension with respect to at least one of the radiation source or the radiation receiver. The third dimension may be perpendicular to the first dimension and the second dimension. The third dimension may be a dimension in which the radiation source is configured to emit radiation.

The operations of flow diagram 1600 may collectively result in the one or more radio-dense calibration markers being positioned in a particular position and orientation with respect to the radiation source, the radiation receiver, and/or a patient whose anatomy is being imaged by the radiographic imaging apparatus. The exact positions to which the radiation source, the radiation receiver, the extension arm, the mounting device, and the post are adjusted to may depend on a type, size, and perspective of the radiograph as well as the habitus of the patient whose anatomy is being imaged using the radiographic imaging device. Further, any of the previously discussed embodiments, features thereof, and/or variations thereof may be used with the embodiment of FIG. 16.

XI. Conclusion

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An apparatus for positioning calibration markers comprising:
   an extension arm connected to one or more radio-dense calibration markers;
   a mounting device removably attachable to a radiographic imaging device and coupled to the extension arm, the mounting device providing for translation of the extension arm with respect to the radiographic imaging device in at least a first dimension; and
   one or more visual alignment features on the mounting device, the one or more visual alignment features configured to align the one or more radio-dense calibration markers relative to the radiographic imaging device;
   wherein the translation of the extension arm repositions the one or more radio-dense calibration markers with respect to the radiographic imaging device.

2. The apparatus of claim 1, wherein the radiographic imaging device comprises a radiation source, and wherein the mounting device is removably attachable to the radiation source of the radiographic imaging device.

3. The apparatus of claim 2, wherein the radiation source comprises one or more targeting lines configured to project one or more corresponding visual reference lines onto a radiation receiver, and wherein the one or more visual alignment features comprise one or more extension lines corresponding to the one or more targeting lines.

4. The apparatus of claim 2, wherein the mounting device is slidably coupled to the radiation source to provide for translation of the mounting device with respect to the radiation source in at least a second dimension, wherein the first dimension is perpendicular to a third dimension in which the radiation source emits radiation, and wherein the second dimension is perpendicular to the first dimension and the third dimension.

5. The apparatus of claim 1, wherein the radiographic imaging device comprises a radiation receiver, and wherein the mounting device is removably attachable to the radiation receiver of the radiographic imaging device.

6. The apparatus of claim 5, wherein the radiation receiver comprises one or more targeting lines, and wherein the one or more visual alignment features are configured to align with the one or more targeting lines.

7. The apparatus of claim 5, wherein the radiographic imaging device further comprises a radiation source comprising one or more targeting lines configured to project one or more corresponding visual reference lines onto the radiation receiver, and wherein the one or more visual alignment features comprise one or more grooves in the mounting device corresponding to the one or more visual reference lines projected onto the radiation receiver.

8. The apparatus of claim 5, wherein the mounting device is slidably coupled to the radiation receiver to provide for translation of the mounting device with respect to the radiation receiver in at least a second dimension, wherein the first dimension is perpendicular to a third dimension in which the radiation receiver receives radiation, and wherein the second dimension is perpendicular to the first dimension and the third dimension.

9. The apparatus of claim 1, further comprising:
a fastening mechanism coupling the extension arm to the mounting device, the fastening mechanism providing for (i) retention of the extension arm in a fixed position with respect to the mounting device when the fastening mechanism is in a first operational configuration and (ii) translation of the extension arm with respect to the radiographic imaging device in at least the first dimension when the fastening mechanism is in a second operational configuration.

10. The apparatus of claim 1, further comprising:
a post coupling the extension arm to the mounting device, the post providing for translation of the extension arm with respect to the radiographic imaging device in at least a second dimension, wherein the second dimension is a dimension in which a radiation source of the radiographic imaging device emits radiation, and wherein the first dimension is perpendicular to the second dimension.

11. The apparatus of claim 10, further comprising:
a fastening mechanism coupling the post to the mounting device, the fastening mechanism providing for (i) retention of the post in a fixed position with respect to the mounting device when the fastening mechanism is in a first operational configuration and (ii) translation of the post with respect to the radiographic imaging device in at least the second dimension when the fastening mechanism is in a second operational configuration.

12. The apparatus of claim 11, wherein the fastening mechanism is a first fastening mechanism, the apparatus further comprising:
a second fastening mechanism coupling the extension arm to the post, the second fastening mechanism providing for (i) retention of the extension arm in a fixed position with respect to the post when the second fastening mechanism is in a first operational configuration and (ii) translation of the extension arm with respect to the post in at least the first dimension when the fastening mechanism is in a second operational configuration.

13. The apparatus of claim 1, wherein the extension arm comprises a radiolucent material that, when exposed to radiation from a radiation source of the radiographic imaging device, does not produce an image of the extension arm on a radiation receiver of the radiographic imaging device.

14. The apparatus of claim 1, wherein the one or more radio-dense calibration markers comprise two or more calibration markers each having at least one known dimension, and wherein the two or more calibration markers are separated from each other by a known distance.

15. The apparatus of claim 1, wherein the one or more radio-dense calibration markers comprise two or more calibration markers having different radio-densities, wherein the radio-density of a respective calibration marker of the two or more calibration markers corresponds to intensity of an image of the respective marker produced on a radiation receiver of the radiographic imaging device.

16. The apparatus of claim 1, wherein the radio-dense calibration markers are radiopaque.

17. A means for positioning marking means comprising:
an extension arm connected to one or more radio-dense marking means;
a mounting means removably attachable to a radiographic imaging device and coupled to the extension arm, the mounting means providing for translation of the extension arm with respect to the radiographic imaging device in at least a first dimension; and
visual alignment means on the mounting means, the visual alignment means configured to align the one or more radio-dense marking means relative to the radiographic imaging device;
wherein the translation of the extension arm repositions the one or more radio-dense marking means with respect to the radiographic imaging device.

18. The means of claim 17, further comprising:
a post coupling the extension arm to the mounting means, the post providing for translation of the extension arm with respect to the radiographic imaging device in at least a second dimension, wherein the second dimension is a dimension in which a radiation source of the radiographic imaging device emits radiation, and wherein the first dimension is perpendicular to the second dimension.

19. The means of claim 17, further comprising:
a fastening means coupling the extension arm to the mounting means, the fastening means providing for (i) retention of the extension arm in a fixed position with respect to the mounting means when the fastening mechanism is in a first operational configuration and (ii) translation of the extension arm with respect to the radiographic imaging device in at least the first dimension when the fastening means is in a second operational configuration.

20. A method of positioning one or more calibration markers, comprising:
positioning a radiation source and a radiation receiver in a first orientation with respect to one another;
positioning an extension arm connected to one or more radio-dense calibration markers to align, in at least a first dimension, one or more alignment features of the extension arm with at least one of the radiation source or the radiation receiver;
positioning a mounting device removably attaching the extension arm to at least one of the radiation source or the radiation receiver to align, in at least a second dimension perpendicular to the first dimension, one or more alignment features of the mounting device with at least one of the radiation source or the radiation receiver; and adjusting a length of a post coupling the extension arm to the mounting device to position the one or more calibration markers in a third dimension with respect to at least one of the radiation source or the radiation receiver, wherein the third dimension is perpendicular to the first dimension and the second dimension.

\* \* \* \* \*